(12) United States Patent
Ashraf et al.

(10) Patent No.: US 11,998,427 B2
(45) Date of Patent: Jun. 4, 2024

(54) NONWOVEN WEBS WITH VISUALLY DISCERNIBLE PATTERNS

(71) Applicant: The Procter & Gamble Company, Cincinnati, OH (US)

(72) Inventors: Arman Ashraf, Mason, OH (US); Alizha V. Smith, Wyoming, OH (US); Christopher S. Cameron, Cincinnati, OH (US); Nayda Liz Ramos Medina, Cincinnati, OH (US); Vanessa M. Melendez, Cincinnati, OH (US); Brittany D. Canfield, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 821 days.

(21) Appl. No.: 16/575,706

(22) Filed: Sep. 19, 2019

(65) Prior Publication Data

US 2020/0100956 A1 Apr. 2, 2020

Related U.S. Application Data

(60) Provisional application No. 62/821,485, filed on Mar. 21, 2019, provisional application No. 62/737,367, filed on Sep. 27, 2018.

(51) Int. Cl.
*A61F 13/511* (2006.01)
*A61F 13/15* (2006.01)
(Continued)

(52) U.S. Cl.
CPC ........ *A61F 13/15585* (2013.01); *A61F 13/49* (2013.01); *A61F 13/51104* (2013.01);
(Continued)

(58) Field of Classification Search
None
See application file for complete search history.

(56) References Cited

U.S. PATENT DOCUMENTS 2,697,678 A * 12/1954 Ness ........................ D04H 1/66
156/229
2,705,498 A * 4/1955 Johnson ................... D04H 1/66
604/377
(Continued)

FOREIGN PATENT DOCUMENTS

CN 1066968 A * 12/1992 ......... A44B 18/0011
CN 1685099 10/2005
(Continued)

OTHER PUBLICATIONS

Machine Translation of CN-101914838-A, Dec. 2010 (Year: 2010).*
(Continued)

*Primary Examiner* — Jeffrey A Vonch
(74) *Attorney, Agent, or Firm* — Christian M. Best

(57) ABSTRACT

A nonwoven web for an absorbent article is provided. The nonwoven web comprises a first surface, a second surface, and a visually discernible pattern of three-dimensional features on the first surface or the second surface. The three-dimensional features comprise one or more first regions and a plurality of second regions. The one or more first regions are different than the plurality of second regions in a value of an average intensive property. The one or more first regions comprise a first line, a second line, and a third line extending at least partially intermediate the first line and the second line. The first line and the second line extend in substantially the same direction. The third line extends in a direction transverse to the first line and the second line.

17 Claims, 25 Drawing Sheets

(51) Int. Cl.

| | |
|---|---|
| *A61F 13/49* | (2006.01) |
| *A61F 13/512* | (2006.01) |
| *A61F 13/513* | (2006.01) |
| *A61F 13/514* | (2006.01) |
| *B32B 3/26* | (2006.01) |
| *B32B 3/30* | (2006.01) |
| *D04H 3/16* | (2006.01) |
| *A61F 13/84* | (2006.01) |
| *B32B 3/28* | (2006.01) |
| *B32B 5/02* | (2006.01) |
| *B32B 7/02* | (2019.01) |
| *B32B 7/12* | (2006.01) |

(52) U.S. Cl.
 CPC .... *A61F 13/5126* (2013.01); *A61F 13/51394* (2013.01); *A61F 13/51401* (2013.01); *A61F 13/51476* (2013.01); *A61F 13/51496* (2013.01); *B32B 3/26* (2013.01); *B32B 3/30* (2013.01); *D04H 3/16* (2013.01); *A61F 2013/51178* (2013.01); *A61F 2013/5127* (2013.01); *A61F 2013/51452* (2013.01); *A61F 2013/51486* (2013.01); *A61F 2013/8497* (2013.01); *B32B 3/263* (2013.01); *B32B 3/28* (2013.01); *B32B 5/022* (2013.01); *B32B 7/02* (2013.01); *B32B 7/12* (2013.01); *B32B 2307/7265* (2013.01); *B32B 2555/02* (2013.01); *Y10T 428/2457* (2015.01); *Y10T 428/24587* (2015.01); *Y10T 428/24603* (2015.01); *Y10T 428/24636* (2015.01); *Y10T 428/24669* (2015.01); *Y10T 428/24678* (2015.01); *Y10T 428/24702* (2015.01); *Y10T 442/60* (2015.04); *Y10T 442/681* (2015.04)

(56) References Cited

U.S. PATENT DOCUMENTS

| | | | | |
|---|---|---|---|---|
| 2,705,687 | A | * | 4/1955 | Peterson .................. C10B 49/00 2/243.1 |
| 3,673,026 | A | * | 6/1972 | Brown ...................... B31F 1/07 156/181 |
| 3,727,615 | A | * | 4/1973 | Duchane ............... A61F 13/513 604/372 |
| 4,079,739 | A | * | 3/1978 | Whitehead ........ A61F 13/51108 604/389 |
| 4,333,979 | A | | 6/1982 | Sciaraffa et al. |
| 4,451,520 | A | | 5/1984 | Tecl et al. |
| 4,493,868 | A | * | 1/1985 | Meitner .................... B32B 5/26 156/290 |
| 4,741,941 | A | | 5/1988 | Englebert et al. |
| 4,970,104 | A | | 11/1990 | Radwanski |
| D319,349 | S | * | 8/1991 | Schultz ............................. D5/20 |
| 5,180,534 | A | | 1/1993 | Thomas et al. |
| 5,188,649 | A | | 2/1993 | Macedo et al. |
| 5,230,851 | A | | 7/1993 | Thomas |
| 5,254,194 | A | | 10/1993 | Ott et al. |
| 5,256,231 | A | | 10/1993 | Gorman et al. |
| 5,318,741 | A | | 6/1994 | Thomas |
| 5,326,612 | A | | 7/1994 | Goulait et al. |
| 5,334,289 | A | | 8/1994 | Trokhan et al. |
| 5,340,372 | A | | 8/1994 | Macedo et al. |
| 5,354,591 | A | | 10/1994 | Ott et al. |
| D354,853 | S | * | 1/1995 | Schulz ............................ D5/53 |
| D354,854 | S | * | 1/1995 | Schulz ............................ D5/53 |
| D354,855 | S | * | 1/1995 | Schulz ............................ D5/53 |
| D354,856 | S | * | 1/1995 | Schulz ............................ D5/53 |
| 5,389,470 | A | | 2/1995 | Parker et al. |
| 5,399,174 | A | * | 3/1995 | Yeo ........................ D04H 3/12 604/366 |
| 5,407,439 | A | | 4/1995 | Goulait et al. |
| D361,895 | S | * | 9/1995 | Arnone ........................... D5/53 |
| 5,470,417 | A | | 11/1995 | Goulait |
| 5,514,523 | A | | 5/1996 | Trokhan et al. |
| 5,540,673 | A | | 7/1996 | Thomas et al. |
| 5,547,531 | A | | 8/1996 | Allen et al. |
| 5,569,233 | A | | 10/1996 | Goulait |
| 5,573,830 | A | * | 11/1996 | Schulz .................... B31F 1/07 428/152 |
| 5,575,874 | A | * | 11/1996 | Griesbach, III .. A61F 13/51104 156/181 |
| 5,595,567 | A | | 1/1997 | King et al. |
| 5,599,420 | A | | 2/1997 | Yeo et al. |
| 5,605,729 | A | | 2/1997 | Mody et al. |
| 5,610,511 | A | | 3/1997 | Parker |
| 5,611,791 | A | | 3/1997 | Gorman et al. |
| 5,614,281 | A | | 3/1997 | Jackson et al. |
| 5,615,460 | A | * | 4/1997 | Weirich ................ A61F 13/627 24/446 |
| 5,616,394 | A | | 4/1997 | Gorman et al. |
| 5,620,779 | A | * | 4/1997 | Levy ..................... D04H 1/549 428/167 |
| 5,628,097 | A | | 5/1997 | Benson et al. |
| 5,643,397 | A | | 7/1997 | Gorman et al. |
| 5,643,653 | A | | 7/1997 | Griesbach, III et al. |
| 5,647,864 | A | | 7/1997 | Allen et al. |
| 5,699,593 | A | | 12/1997 | Jackson |
| 5,714,107 | A | | 2/1998 | Levy et al. |
| 5,725,927 | A | | 3/1998 | Zilg et al. |
| 5,762,645 | A | | 6/1998 | Peck et al. |
| 5,773,120 | A | | 6/1998 | Deka et al. |
| 5,817,394 | A | | 10/1998 | Alikhan et al. |
| 5,825,174 | A | | 10/1998 | Parker |
| 5,830,298 | A | | 11/1998 | Jackson |
| D402,475 | S | * | 12/1998 | Mattheeussen ................. D5/35 |
| D403,763 | S | * | 1/1999 | Lynard ........................ D24/125 |
| D403,764 | S | * | 1/1999 | Lynard ........................ D24/125 |
| 5,858,504 | A | | 1/1999 | Steven |
| 5,858,515 | A | | 1/1999 | Stokes et al. |
| D406,791 | S | * | 3/1999 | Schulz ............................ D5/27 |
| 5,888,607 | A | | 3/1999 | Seth et al. |
| D407,902 | S | * | 4/1999 | Schulz ............................ D5/53 |
| 5,895,623 | A | | 4/1999 | Trokhan et al. |
| 5,897,541 | A | * | 4/1999 | Uitenbroek ......... A61F 13/5148 604/385.21 |
| 5,916,661 | A | | 6/1999 | Benson et al. |
| 5,964,742 | A | * | 10/1999 | McCormack .......... D04H 1/54 604/380 |
| 5,997,981 | A | | 12/1999 | Mccormack et al. |
| D426,889 | S | * | 6/2000 | Bissah ............................. D5/37 |
| D428,267 | S | | 7/2000 | Sayovitz et al. |
| D431,371 | S | * | 10/2000 | Ingalls ............................ D5/57 |
| 6,129,972 | A | * | 10/2000 | McNeil .................. B32B 29/00 428/154 |
| 6,139,941 | A | | 10/2000 | Jankevics et al. |
| 6,140,551 | A | * | 10/2000 | Niemeyer ......... A61F 13/51496 604/383 |
| D433,572 | S | * | 11/2000 | Bissah ............................. D5/58 |
| 6,150,002 | A | | 11/2000 | Varona |
| 6,162,522 | A | | 12/2000 | Deka et al. |
| 6,197,404 | B1 | | 3/2001 | Varona |
| 6,231,555 | B1 | * | 5/2001 | Lynard ................ A61F 13/5126 604/385.16 |
| 6,238,767 | B1 | | 5/2001 | Mccormack et al. |
| 6,261,666 | B1 | * | 7/2001 | Enderby .................. B31F 1/07 428/156 |
| D448,078 | S | * | 9/2001 | Deoliveira .................... D24/124 |
| D448,478 | S | * | 9/2001 | Deoliveira .................... D24/124 |
| 6,319,239 | B1 | * | 11/2001 | Daniels ................. A61F 13/539 604/385.01 |
| 6,319,455 | B1 | | 11/2001 | Kauschke et al. |
| 6,331,268 | B1 | | 12/2001 | Kauschke et al. |
| 6,331,345 | B1 | | 12/2001 | Kauschke et al. |
| 6,344,111 | B1 | * | 2/2002 | Wilhelm ............... D21H 25/005 428/179 |
| 6,361,638 | B2 | | 3/2002 | Takai et al. |
| 6,383,431 | B1 | | 5/2002 | Dobrin et al. |
| 6,395,957 | B1 | | 5/2002 | Chen et al. |
| 6,436,512 | B1 | | 8/2002 | Kauschke et al. |

(56) References Cited

U.S. PATENT DOCUMENTS

| | | | |
|---|---|---|---|
| 6,520,330 B1 * | 2/2003 | Batra | A47K 10/42 |
| | | | 206/459.5 |
| 6,572,722 B1 * | 6/2003 | Pratt | B31F 1/07 |
| | | | 156/290 |
| 6,589,638 B1 | 7/2003 | Mccormack et al. | |
| 6,592,697 B2 | 7/2003 | Pike et al. | |
| 6,610,390 B1 * | 8/2003 | Kauschke | B32B 25/10 |
| | | | 442/325 |
| 6,623,469 B1 | 9/2003 | Thomas | |
| 6,632,504 B1 | 10/2003 | Gillespie et al. | |
| 6,637,079 B1 | 10/2003 | Goulait et al. | |
| 6,673,418 B1 | 1/2004 | DeOlivera et al. | |
| 6,743,321 B2 | 6/2004 | Guralski et al. | |
| 6,749,719 B2 * | 6/2004 | Burazin | D21F 1/0027 |
| | | | 162/207 |
| 6,756,327 B2 | 6/2004 | Martin | |
| 6,770,065 B1 * | 8/2004 | Sasaki | A44B 18/0049 |
| | | | 604/385.01 |
| 6,787,000 B2 * | 9/2004 | Burazin | D21F 1/0027 |
| | | | 162/902 |
| 6,818,802 B2 | 11/2004 | Takai et al. | |
| 6,838,154 B1 | 1/2005 | Varona et al. | |
| 6,849,142 B1 | 2/2005 | Goulait et al. | |
| 6,921,570 B2 | 7/2005 | Belau et al. | |
| 6,955,668 B2 | 10/2005 | Imberg et al. | |
| 6,969,377 B2 | 11/2005 | Koele et al. | |
| 7,156,937 B2 | 1/2007 | Provost et al. | |
| 7,162,749 B2 | 1/2007 | Carbone et al. | |
| 7,207,979 B2 | 4/2007 | Price et al. | |
| 7,276,642 B2 | 10/2007 | Belau | |
| 7,371,919 B1 | 5/2008 | Busam et al. | |
| 7,407,496 B2 | 8/2008 | Petersen | |
| 7,465,366 B2 | 12/2008 | Provost et al. | |
| 7,497,851 B2 | 3/2009 | Koele et al. | |
| 7,507,463 B2 | 3/2009 | Noda et al. | |
| 7,544,628 B2 | 6/2009 | Stupperich et al. | |
| 7,547,469 B2 | 6/2009 | Provost | |
| 7,553,535 B2 | 6/2009 | Noda et al. | |
| 7,562,426 B2 | 7/2009 | Barker et al. | |
| 7,662,462 B2 | 2/2010 | Noda et al. | |
| 7,789,870 B2 | 9/2010 | Horn et al. | |
| 7,790,264 B2 | 9/2010 | Lester, Jr. et al. | |
| 7,805,818 B2 | 10/2010 | Horn et al. | |
| 7,862,550 B2 | 1/2011 | Koele et al. | |
| 7,895,718 B2 | 3/2011 | Horn | |
| 7,897,240 B2 | 3/2011 | Noda et al. | |
| 7,954,213 B2 | 6/2011 | Mizutani et al. | |
| 7,955,549 B2 | 6/2011 | Noda et al. | |
| 7,960,008 B2 | 6/2011 | Lester, Jr. et al. | |
| 7,968,479 B2 | 6/2011 | Welch et al. | |
| 7,981,822 B2 | 7/2011 | Lester, Jr. et al. | |
| 8,002,761 B2 | 8/2011 | Utsunomiya et al. | |
| 8,034,431 B2 | 10/2011 | Seth | |
| 8,123,734 B2 | 2/2012 | Imberg | |
| 8,143,177 B2 | 3/2012 | Noda et al. | |
| 8,183,431 B2 | 5/2012 | Noda et al. | |
| 8,212,103 B2 | 7/2012 | Kingsford et al. | |
| 8,257,333 B2 | 9/2012 | Hancock-Cooke | |
| 8,273,941 B2 | 9/2012 | Uematsu et al. | |
| 8,304,600 B2 | 11/2012 | Noda et al. | |
| 8,323,435 B2 | 12/2012 | Durrance et al. | |
| 8,388,596 B2 | 3/2013 | Horn | |
| 8,426,672 B2 | 4/2013 | Kingsford et al. | |
| 8,562,580 B2 | 10/2013 | Van Gompel et al. | |
| 8,574,209 B2 | 11/2013 | Nishitani et al. | |
| 8,585,666 B2 | 11/2013 | Weisman et al. | |
| 8,590,119 B2 | 11/2013 | Horn | |
| 8,673,097 B2 | 3/2014 | Barker et al. | |
| RE44,842 E | 4/2014 | Lester, Jr. et al. | |
| 8,753,459 B2 | 6/2014 | Provost | |
| 8,758,569 B2 | 6/2014 | Aberg et al. | |
| 8,853,108 B2 | 10/2014 | Ahoniemi et al. | |
| 8,865,965 B2 | 10/2014 | Sato et al. | |
| 8,898,868 B2 | 12/2014 | Horn et al. | |
| 8,906,275 B2 | 12/2014 | Davis et al. | |
| 9,056,032 B2 | 6/2015 | Ashraf et al. | |
| 9,078,793 B2 | 7/2015 | Barker | |
| 9,084,701 B2 | 7/2015 | Medina et al. | |
| 9,091,005 B2 | 7/2015 | Masuda et al. | |
| 9,095,477 B2 | 8/2015 | Yamaguchi et al. | |
| 9,114,045 B2 | 8/2015 | Sakaguchi et al. | |
| 9,125,775 B2 | 9/2015 | Durrance et al. | |
| 9,156,229 B2 | 10/2015 | Yoda et al. | |
| 9,205,005 B2 | 12/2015 | Kikuchi et al. | |
| 9,205,006 B2 | 12/2015 | Cheng et al. | |
| 9,259,059 B2 | 2/2016 | Horn et al. | |
| 9,259,367 B2 | 2/2016 | Magee et al. | |
| RE45,946 E | 3/2016 | Lester, Jr. et al. | |
| 9,408,761 B2 | 8/2016 | Xu | |
| 9,453,303 B2 | 9/2016 | Aberg et al. | |
| 9,468,265 B2 | 10/2016 | Horn | |
| D772,583 S | 11/2016 | Hannen et al. | |
| 9,504,610 B2 | 11/2016 | Cheng et al. | |
| 9,662,248 B2 | 5/2017 | Van Gompel et al. | |
| 9,732,454 B2 | 8/2017 | Davis et al. | |
| 9,737,441 B2 | 8/2017 | Song et al. | |
| 9,744,085 B2 | 8/2017 | Ashraf et al. | |
| 9,877,876 B2 | 1/2018 | Huang et al. | |
| 9,903,070 B2 | 2/2018 | Mourad et al. | |
| 9,913,764 B2 | 3/2018 | Thomas et al. | |
| 9,974,700 B2 | 5/2018 | Cheng et al. | |
| 10,016,316 B2 | 7/2018 | Sakaguchi et al. | |
| 10,016,319 B2 | 7/2018 | Cheng et al. | |
| 10,028,866 B2 | 7/2018 | Xu | |
| 10,190,244 B2 | 1/2019 | Ashraf et al. | |
| D859,008 S * | 9/2019 | Olson | D5/59 |
| D860,656 S * | 9/2019 | Barai | D5/53 |
| 11,918,442 B2 * | 3/2024 | Smith | A61F 13/49 |
| 2001/0008683 A1 * | 7/2001 | Takai | D04H 1/558 |
| | | | 428/196 |
| 2001/0029141 A1 | 10/2001 | Mizutani et al. | |
| 2002/0034914 A1 * | 3/2002 | De Leon | D04H 1/49 |
| | | | 28/103 |
| 2002/0068150 A1 * | 6/2002 | Taneichi | D04H 1/559 |
| | | | 428/137 |
| 2002/0103469 A1 | 8/2002 | Chen et al. | |
| 2002/0150431 A1 | 10/2002 | Ofosu-Asante | |
| 2002/0153271 A1 | 10/2002 | McManus et al. | |
| 2002/0193032 A1 | 12/2002 | Newkirk et al. | |
| 2002/0193774 A1 * | 12/2002 | Otsubo | A61F 13/51464 |
| | | | 604/385.29 |
| 2003/0050615 A1 * | 3/2003 | Sakamoto | A61F 13/5116 |
| | | | 604/367 |
| 2003/0077430 A1 | 4/2003 | Grimm | |
| 2003/0093045 A1 | 5/2003 | Jensen | |
| 2003/0116259 A1 | 6/2003 | Sayovitz et al. | |
| 2003/0119404 A1 | 6/2003 | Belau et al. | |
| 2003/0125687 A1 | 7/2003 | Gubernick et al. | |
| 2003/0139719 A1 * | 7/2003 | Nanaumi | A61F 13/533 |
| | | | 604/374 |
| 2003/0203162 A1 | 10/2003 | Christopher et al. | |
| 2003/0203691 A1 | 10/2003 | Fenwick et al. | |
| 2003/0211802 A1 | 11/2003 | Keck et al. | |
| 2004/0029479 A1 * | 2/2004 | Snider | D04H 1/495 |
| | | | 28/104 |
| 2004/0059309 A1 | 3/2004 | Nortman | |
| 2004/0063369 A1 | 4/2004 | Ahn et al. | |
| 2004/0158957 A1 * | 8/2004 | Horn | A44B 18/0011 |
| | | | 24/442 |
| 2004/0193135 A1 | 9/2004 | Van Gompel | |
| 2004/0230171 A1 | 11/2004 | Ando | |
| 2004/0241399 A1 * | 12/2004 | Marmon | D04H 1/559 |
| | | | 428/196 |
| 2005/0147785 A1 | 7/2005 | Ahn et al. | |
| 2005/0148971 A1 | 7/2005 | Kuroda et al. | |
| 2005/0196580 A1 | 9/2005 | Provost | |
| 2005/0196583 A1 | 9/2005 | Provost | |
| 2005/0217092 A1 | 10/2005 | Barker et al. | |
| 2006/0019055 A1 | 1/2006 | Lester et al. | |
| 2006/0021536 A1 | 2/2006 | Song et al. | |
| 2006/0080810 A1 | 4/2006 | Horn et al. | |
| 2006/0087053 A1 | 4/2006 | O'Donnell et al. | |

(56) References Cited

U.S. PATENT DOCUMENTS

| | | |
|---|---|---|
| 2006/0105075 A1 | 5/2006 | Otsubo |
| 2006/0189954 A1 | 8/2006 | Kudo et al. |
| 2006/0286343 A1 | 12/2006 | Curro et al. |
| 2007/0026753 A1 | 2/2007 | Neely et al. |
| 2007/0045143 A1 | 3/2007 | Clough et al. |
| 2007/0045144 A1 | 3/2007 | Wheeler et al. |
| 2007/0049889 A1 | 3/2007 | Larson et al. |
| 2007/0128411 A1* | 6/2007 | Kawai .............. B32B 5/022 428/218 |
| 2007/0178273 A1 | 8/2007 | Provost et al. |
| 2007/0179466 A1 | 8/2007 | Tremblay et al. |
| 2007/0298214 A1 | 12/2007 | Noda et al. |
| 2007/0298667 A1 | 12/2007 | Noda et al. |
| 2008/0026178 A1* | 1/2008 | Stupperich .......... D04H 11/00 428/99 |
| 2008/0086104 A1 | 4/2008 | Karlsson |
| 2008/0102725 A1 | 5/2008 | Lacey et al. |
| 2008/0108967 A1 | 5/2008 | Muzushima et al. |
| 2008/0149292 A1 | 6/2008 | Scherb |
| 2008/0161765 A1 | 7/2008 | Morman et al. |
| 2008/0260989 A1* | 10/2008 | Lester ................ D04H 11/08 428/100 |
| 2009/0169827 A1 | 7/2009 | Dharmadhikary et al. |
| 2009/0240222 A1 | 9/2009 | Tomoko et al. |
| 2009/0280274 A1 | 11/2009 | Herlein |
| 2010/0015386 A1* | 1/2010 | Baldauf .............. A61F 13/627 428/99 |
| 2010/0030176 A1* | 2/2010 | Beckert .............. A61F 13/622 604/389 |
| 2010/0036346 A1 | 2/2010 | Hammons |
| 2010/0036349 A1 | 2/2010 | Hammons |
| 2010/0048072 A1 | 2/2010 | Kauschke |
| 2010/0286644 A1 | 11/2010 | Li |
| 2010/0298796 A1 | 11/2010 | Horn |
| 2010/0324517 A1 | 12/2010 | Lenhult et al. |
| 2011/0250378 A1 | 10/2011 | Eaton et al. |
| 2011/0250413 A1 | 10/2011 | Lu et al. |
| 2011/0257620 A1 | 10/2011 | Horn et al. |
| 2011/0313385 A1 | 12/2011 | Hammons et al. |
| 2012/0004633 A1 | 1/2012 | Marcelo et al. |
| 2012/0022488 A1 | 1/2012 | Otsubo et al. |
| 2012/0029454 A1 | 2/2012 | Li et al. |
| 2012/0089112 A1 | 4/2012 | Horn et al. |
| 2012/0095429 A1 | 4/2012 | Kobayashi |
| 2012/0095431 A1 | 4/2012 | Tsai |
| 2012/0177886 A1* | 7/2012 | Kanya .............. A61F 13/51476 428/156 |
| 2012/0189814 A1 | 7/2012 | Coslett et al. |
| 2012/0196091 A1 | 8/2012 | Mizutani et al. |
| 2012/0226249 A1 | 9/2012 | Prodoehl et al. |
| 2012/0231206 A1 | 9/2012 | Thompson, Jr. et al. |
| 2012/0245550 A1* | 9/2012 | Sakaguchi .......... A61F 13/627 604/391 |
| 2012/0315440 A1* | 12/2012 | Ichikawa ............ D04H 1/54 428/156 |
| 2012/0316532 A1* | 12/2012 | McCormick ...... A61F 13/51104 604/385.01 |
| 2013/0112584 A1 | 5/2013 | Gaspari et al. |
| 2013/0138073 A1 | 5/2013 | Horn et al. |
| 2013/0139960 A1 | 6/2013 | Maruyama et al. |
| 2013/0167305 A1* | 7/2013 | Weisman .............. C11D 17/047 510/439 |
| 2013/0171421 A1* | 7/2013 | Weisman .............. D01F 1/10 264/103 |
| 2013/0178815 A1* | 7/2013 | Ohashi .............. A61F 13/51108 604/380 |
| 2013/0236700 A1* | 9/2013 | Yamanaka ........ A61F 13/15731 264/505 |
| 2013/0253461 A1* | 9/2013 | Xu .................... A61F 13/51121 428/156 |
| 2013/0261579 A1* | 10/2013 | Hwang ............. A61F 13/53747 604/378 |
| 2013/0310797 A1 | 11/2013 | Zink |
| 2013/0320584 A1 | 12/2013 | Davis et al. |
| 2014/0000070 A1 | 1/2014 | Ashraf et al. |
| 2014/0000784 A1 | 1/2014 | Rane et al. |
| 2014/0037906 A1* | 2/2014 | Polosa ................ D04H 1/54 428/167 |
| 2014/0039438 A1 | 2/2014 | Ferrer et al. |
| 2014/0044934 A1 | 2/2014 | Bills et al. |
| 2014/0088535 A1* | 3/2014 | Xu .................... A61F 13/15731 604/366 |
| 2014/0127460 A1 | 5/2014 | Xu et al. |
| 2014/0234575 A1 | 8/2014 | Mitsuno et al. |
| 2014/0259483 A1 | 9/2014 | Cheng et al. |
| 2014/0272261 A1 | 9/2014 | Udengaard et al. |
| 2014/0272359 A1 | 9/2014 | Cheng et al. |
| 2014/0276517 A1 | 9/2014 | Chester et al. |
| 2014/0296815 A1 | 10/2014 | Takken et al. |
| 2014/0305570 A1 | 10/2014 | Matsunaga et al. |
| 2014/0324009 A1 | 10/2014 | Lee et al. |
| 2014/0343526 A1* | 11/2014 | Knapmeyer ....... D04H 1/43828 428/196 |
| 2015/0038933 A1 | 2/2015 | Day et al. |
| 2015/0057627 A1* | 2/2015 | Noda ................ A61F 13/5126 604/378 |
| 2015/0107063 A1* | 4/2015 | Baldauf .............. B32B 5/26 24/449 |
| 2015/0173967 A1 | 6/2015 | Kreuzer et al. |
| 2015/0182387 A1 | 7/2015 | Ferrer et al. |
| 2015/0238373 A1 | 8/2015 | Ramos-Medina et al. |
| 2015/0250662 A1 | 9/2015 | Isele et al. |
| 2015/0250663 A1* | 9/2015 | Wagner ................ A61F 13/512 604/378 |
| 2015/0282999 A1* | 10/2015 | Arizti ................ A61F 13/8405 604/385.01 |
| 2016/0007819 A1 | 1/2016 | Cheng et al. |
| 2016/0067119 A1 | 3/2016 | Weisman et al. |
| 2016/0101003 A1 | 4/2016 | Jennewein et al. |
| 2016/0106633 A1 | 4/2016 | Nagata et al. |
| 2016/0129661 A1 | 5/2016 | Arora et al. |
| 2016/0136009 A1 | 5/2016 | Weisman et al. |
| 2016/0270976 A1 | 9/2016 | Minoguchi et al. |
| 2016/0324698 A1 | 11/2016 | Xu et al. |
| 2016/0362825 A1* | 12/2016 | Novarino .............. D04H 1/559 |
| 2016/0367408 A1 | 12/2016 | Coslett et al. |
| 2017/0000663 A1 | 1/2017 | Xu et al. |
| 2017/0014280 A1 | 1/2017 | Moritani |
| 2017/0014281 A1 | 1/2017 | Xie et al. |
| 2017/0014291 A1 | 1/2017 | Kie et al. |
| 2017/0027774 A1 | 2/2017 | Ashraf et al. |
| 2017/0029993 A1 | 2/2017 | Ashraf et al. |
| 2017/0029994 A1* | 2/2017 | Ashraf .............. A61F 13/51104 |
| 2017/0056256 A1 | 3/2017 | Smith et al. |
| 2017/0121873 A1 | 5/2017 | Kimura et al. |
| 2017/0151101 A1* | 6/2017 | Isele ................ A61F 13/51121 |
| 2017/0151103 A1 | 6/2017 | Bianchi |
| 2017/0191198 A1* | 7/2017 | Ashraf .............. D01D 5/0985 |
| 2017/0202318 A1 | 7/2017 | Morishita et al. |
| 2017/0246052 A1 | 8/2017 | Ludwig |
| 2017/0258650 A1 | 9/2017 | Rosati et al. |
| 2017/0281428 A1 | 10/2017 | Mueller et al. |
| 2017/0304123 A1 | 10/2017 | Ferrer et al. |
| 2017/0333263 A1* | 11/2017 | Tashiro ............ A61F 13/53717 |
| 2017/0333265 A1* | 11/2017 | Hanao .............. A61F 13/531 |
| 2017/0335498 A1 | 11/2017 | Hansen et al. |
| 2017/0348163 A1 | 12/2017 | Lakso et al. |
| 2018/0133070 A1 | 5/2018 | Thomas et al. |
| 2018/0168893 A1 | 6/2018 | Ashraf et al. |
| 2018/0214318 A1 | 8/2018 | Ashraf et al. |
| 2018/0214321 A1 | 8/2018 | Ashraf et al. |
| 2018/0216269 A1 | 8/2018 | Ashraf et al. |
| 2018/0216270 A1 | 8/2018 | Ashraf et al. |
| 2018/0216271 A1 | 8/2018 | Ashraf et al. |
| 2018/0222143 A1 | 8/2018 | Gilbert et al. |
| 2018/0228659 A1 | 8/2018 | Conrad et al. |
| 2018/0229216 A1 | 8/2018 | Smith et al. |
| 2018/0263830 A1 | 9/2018 | Uchida et al. |
| 2018/0281296 A1 | 10/2018 | Uchida et al. |
| 2019/0003079 A1 | 1/2019 | Ashraf et al. |
| 2019/0003080 A1 | 1/2019 | Ashraf et al. |
| 2019/0070042 A1* | 3/2019 | LaVon ................ D04H 3/12 |
| 2019/0112737 A1 | 4/2019 | Ashraf et al. |

(56) References Cited

U.S. PATENT DOCUMENTS

| | | | |
|---|---|---|---|
| 2019/0125594 A1* | 5/2019 | Angeli | B32B 5/022 |
| 2019/0161897 A1* | 5/2019 | Mecl | D04H 3/14 |
| 2019/0254882 A1 | 8/2019 | Trennepohl et al. | |
| 2019/0290503 A1 | 9/2019 | Mullane et al. | |
| 2020/0054501 A1 | 2/2020 | Seto et al. | |
| 2020/0100949 A1 | 4/2020 | Smith et al. | |
| 2020/0100955 A1* | 4/2020 | Smith | A61F 13/51476 |
| 2020/0297555 A1 | 9/2020 | Ramos Medina et al. | |

FOREIGN PATENT DOCUMENTS

| | | | | |
|---|---|---|---|---|
| CN | 101208063 A | | 6/2008 | |
| CN | 101914838 A | * | 12/2010 | |
| CN | 106943241 A | | 7/2017 | |
| CN | 106948086 A | * | 7/2017 | D04H 1/54 |
| DE | 102004053805 B3 | * | 8/2006 | A44B 18/0011 |
| DE | 202006021198 U1 | * | 10/2013 | A61F 13/5622 |
| EP | 882828 A1 | * | 12/1998 | A44B 18/0011 |
| EP | 0882828 A1 | | 12/1998 | |
| EP | 2660377 | | 4/2014 | |
| EP | 2821043 A1 | * | 1/2015 | A61F 13/51104 |
| JP | 57167442 A | * | 10/1982 | |
| JP | 61048359 A | * | 3/1986 | |
| JP | 10272152 A | * | 10/1998 | A61F 13/512 |
| JP | 2001-008713 | | 1/2001 | |
| JP | 2002-030559 | | 1/2002 | |
| JP | 2002165831 A | | 6/2002 | |
| JP | 2002249965 A | * | 9/2002 | |
| JP | 2003235894 A | * | 8/2003 | |
| JP | 2004-081254 | | 3/2004 | |
| JP | 2004188077 A | * | 7/2004 | |
| JP | 2006-034872 | | 2/2006 | |
| JP | 2006265782 A | * | 10/2006 | |
| JP | 2009-000512 | | 1/2009 | |
| JP | 2009-101091 | | 5/2009 | |
| JP | 2010-024573 | | 2/2010 | |
| JP | 2011-015707 | | 1/2011 | |
| JP | 2011015707 A | * | 1/2011 | |
| JP | 2011137262 A | * | 7/2011 | |
| JP | 2011200337 A | * | 10/2011 | A61F 13/472 |
| JP | 2012136785 A | * | 7/2012 | D04H 1/54 |
| JP | 2012239531 A | * | 12/2012 | |
| JP | 2013121486 A | * | 6/2013 | |
| JP | 2013223686 A | * | 10/2013 | A61F 13/4942 |
| JP | 2014-097257 | | 5/2014 | |
| JP | 2014094159 A | | 5/2014 | |
| JP | 2014-188042 | | 10/2014 | |
| JP | 2015043895 A | * | 3/2015 | |
| JP | 2015112306 A | * | 6/2015 | |
| JP | 2015112340 A | * | 6/2015 | |
| JP | 2016067466 A | * | 5/2016 | |
| JP | 2017104197 A | * | 6/2017 | A61F 13/15 |
| JP | 2017196064 A | * | 11/2017 | A61F 13/15 |
| WO | WO-9923905 | | 5/1995 | |
| WO | WO-9611107 | | 4/1996 | |
| WO | WO-9719808 | | 6/1997 | |
| WO | WO-9719808 A1 | * | 6/1997 | A44B 18/0011 |
| WO | WO-0035503 A1 | * | 6/2000 | A61F 13/511 |
| WO | WO-2004029349 A1 | * | 4/2004 | A61F 13/51104 |
| WO | WO-2007096842 | | 8/2007 | |
| WO | WO201286730 | | 6/2012 | |
| WO | WO-2012086766 A1 | * | 6/2012 | D04H 1/54 |
| WO | WO-2012169576 A1 | * | 12/2012 | A61F 13/539 |
| WO | WO201318846 | | 2/2013 | |
| WO | WO-2003015681 | | 2/2013 | |
| WO | WO 2013084977 | | 6/2013 | |
| WO | WO201399625 | | 7/2013 | |
| WO | WO2013145966 | | 10/2013 | |
| WO | WO-2013190831 A1 | * | 12/2013 | A61F 13/5644 |
| WO | WO-2014024643 A1 | * | 2/2014 | A61F 13/15699 |
| WO | WO-2014050310 A1 | * | 4/2014 | A61F 13/51104 |
| WO | WO-2014073637 | | 9/2014 | |
| WO | WO-2016001742 | | 1/2016 | |
| WO | WO-2016092843 A1 | * | 6/2016 | A61F 13/15203 |
| WO | WO-2016098848 A1 | * | 6/2016 | A61F 13/49 |
| WO | WO-2016204131 | | 12/2016 | |
| WO | WO-2016204132 | | 12/2016 | |
| WO | WO-2017006567 A1 | * | 1/2017 | A61F 13/511 |
| WO | WO-2017038030 A1 | * | 3/2017 | A61F 13/511 |
| WO | WO-2017040240 | | 3/2017 | |
| WO | WO-2017105997 | | 6/2017 | |
| WO | WO2017110695 | | 6/2017 | |
| WO | WO-2017131597 A1 | * | 8/2017 | |
| WO | WO-2017148865 | | 9/2017 | |
| WO | WO-2018124996 | | 7/2018 | |

OTHER PUBLICATIONS

Machine Translation of JP-2011137262-A, Jul. 2011 (Year: 2011).*
Machine Translation of JP-2015112306-A, Jun. 2015 (Year: 2015).*
Machine Translation of JP-2002249965-A, Sep. 2002 (Year: 2002).*
All Office Actions, U.S. Appl. No. 16/575,684.
All Office Actions, U.S. Appl. No. 16/575,424.
3D Nonwovens Developments for textured nonwovens; Detlef Frey; http://web.archive.org/web/20170919080326/https://www.reicofil.com/en/pages/3d_nonwovens, Sep. 19, 2017.
International Search Report and Written Opinion, PCT/US2019/051808, date of mailing Dec. 13, 2019.
All Office Actions, U.S. Appl. No. 16/812,632.
All Office Actions; U.S. Appl. No. 18/507,416, filed Nov. 13, 2023.
Unpublished U.S. Appl. No. 18/507,416, filed Nov. 13, 2023, to Alizha V. Smith et al.

* cited by examiner

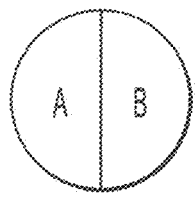 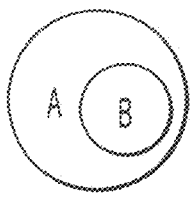 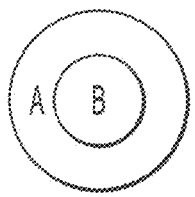
Fig. 20A        Fig. 20B        Fig. 20C
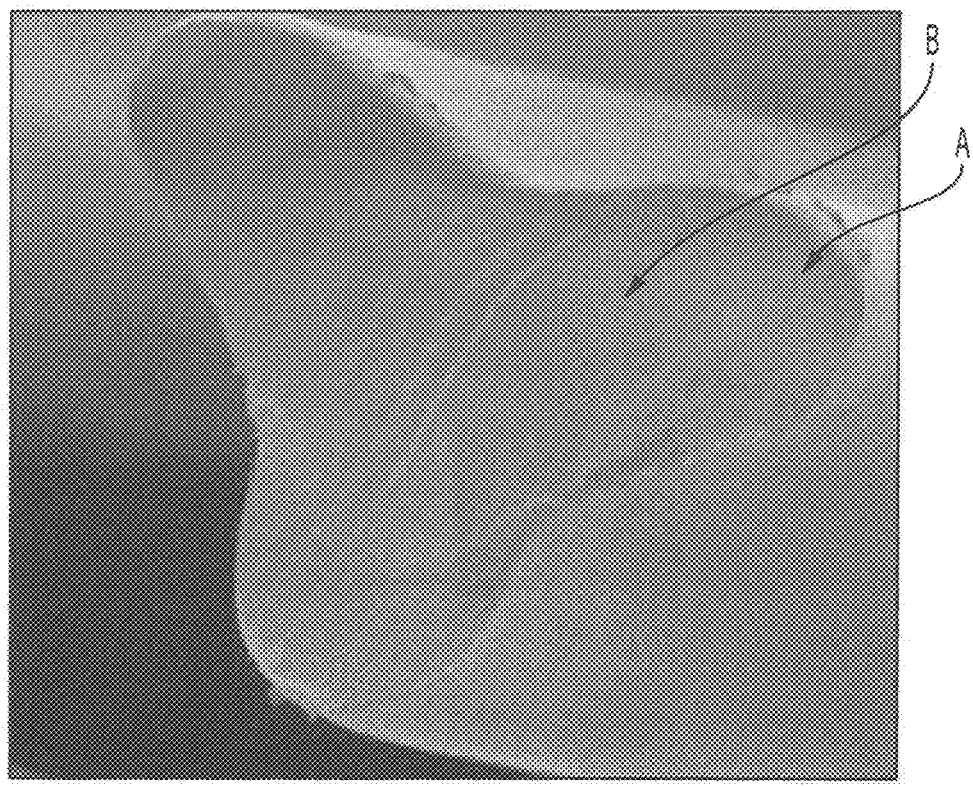
Fig. 21   5 μm

NONWOVEN WEBS WITH VISUALLY DISCERNIBLE PATTERNS

CROSS REFERENCE TO RELATED APPLICATION

This application claims the benefit of U.S. Provisional Patent Application No. 62/737,367, filed Sep. 27, 2018 and U.S. Provisional Patent Application No. 62/821,485, filed Mar. 21, 2019, the entire substance of which are incorporated herein by reference.

FIELD

The present disclosure is directed to nonwoven webs with visually discernible patterns of three-dimensional features. The present disclosure is also directed to nonwoven webs with visually discernible patterns of three-dimensional features for absorbent articles.

BACKGROUND

Nonwoven webs are used in many industries, including the medical, hygiene, and cleaning industries. Absorbent articles comprising nonwoven webs are used in the hygiene industry to contain and absorb bodily exudates (i.e., urine, bowel movements, and menses) in infants, toddlers, children, and adults. Absorbent articles may include, but not be limited to, diapers, pants, adult incontinence products, feminine care products, and absorbent pads. Various components of these absorbent articles comprise nonwoven webs. Some example components that comprise nonwoven webs are outer cover nonwoven materials, topsheets, waistbands, leg cuffs, waist cuffs, ears, belts, and acquisition materials, for example. Consumers desire high quality nonwoven webs that function well for their intended purpose. Manufacturers seek to develop and deliver high quality nonwoven webs as consumers may pay more for absorbent articles with such high quality nonwoven webs. Some factors that consumers attribute to high quality are texture, softness, and having the appearance of being a man-made fabric. As such, nonwoven webs should be improved to deliver against constantly higher expectations consumers have for what would be considered high quality nonwoven webs.

SUMMARY

The present disclosure provides, in part, nonwoven webs with visually discernable patterns of three-dimensional features that have the improved tactile properties, softness, and create a visual appearance of a man-made quilted fabric or blanket. Stated differently, the nonwoven webs of the present disclosure provide a more quilted texture and appearance compared to previous nonwoven webs. The visually discernable patterns of three-dimensional features may comprise one or more first regions and a plurality of second regions. The one or more first regions are areas where the nonwoven webs are low-basis weight, densified, and/or compressed and may contribute to the appearance and tactile perception of stitching or stitch-like consolidation of a quilted fabric. The plurality of second regions are fluffy, high basis weight areas and may contribute to the appearance and tactile perception of soft portions of a quilt in between the stitching. This combination in texture and softness with tactile and visual appearances properties creates premium nonwoven webs that are highly desired by consumers, such as absorbent article consumers.

BRIEF DESCRIPTION OF THE DRAWINGS

The above-mentioned and other features and advantages of the present disclosure, and the manner of attaining them, will become more apparent and the disclosure itself will be better understood by reference to the following description of example forms of the disclosure taken in conjunction with the accompanying drawings, wherein:

FIG. 20A is a schematic drawing illustrating a cross-section of a filament made with a primary component A and a secondary component B in a side-by-side arrangement;

FIG. 20B is a schematic drawing illustrating a cross-section of a filament made with a primary component A and a secondary component B in an eccentric sheath/core arrangement;

FIG. 20C is a schematic drawing illustrating a cross-section of a filament made with a primary component A and a secondary component B in a concentric sheath/core arrangement;

FIG. 21 is a perspective view photograph of a tri-lobal, bicomponent fiber;

DETAILED DESCRIPTION

Various non-limiting forms of the present disclosure will now be described to provide an overall understanding of the principles of the structure, function, manufacture, and use of the nonwoven webs with visually discernable patterns disclosed herein. One or more examples of these non-limiting forms are illustrated in the accompanying drawings. Those of ordinary skill in the art will understand that the nonwoven webs with visually discernable patterns described herein and illustrated in the accompanying drawings are non-limiting example forms and that the scope of the various non-limiting forms of the present disclosure are defined solely by the claims. The features illustrated or described in connection with one non-limiting form may be combined with the features of other non-limiting forms. Such modifications and variations are intended to be included within the scope of the present disclosure.

Prior to a discussion of the nonwoven webs with visually discernable patterns absorbent articles and their components and features will be discussed as one possible use of the nonwoven webs. It will be understood that the nonwoven webs with visually discernable patterns also have other uses in other products, such as in the medical field, the cleaning and/or dusting field, and/or the wipes field, for example.

General Description of an Absorbent Article

Figure 1:
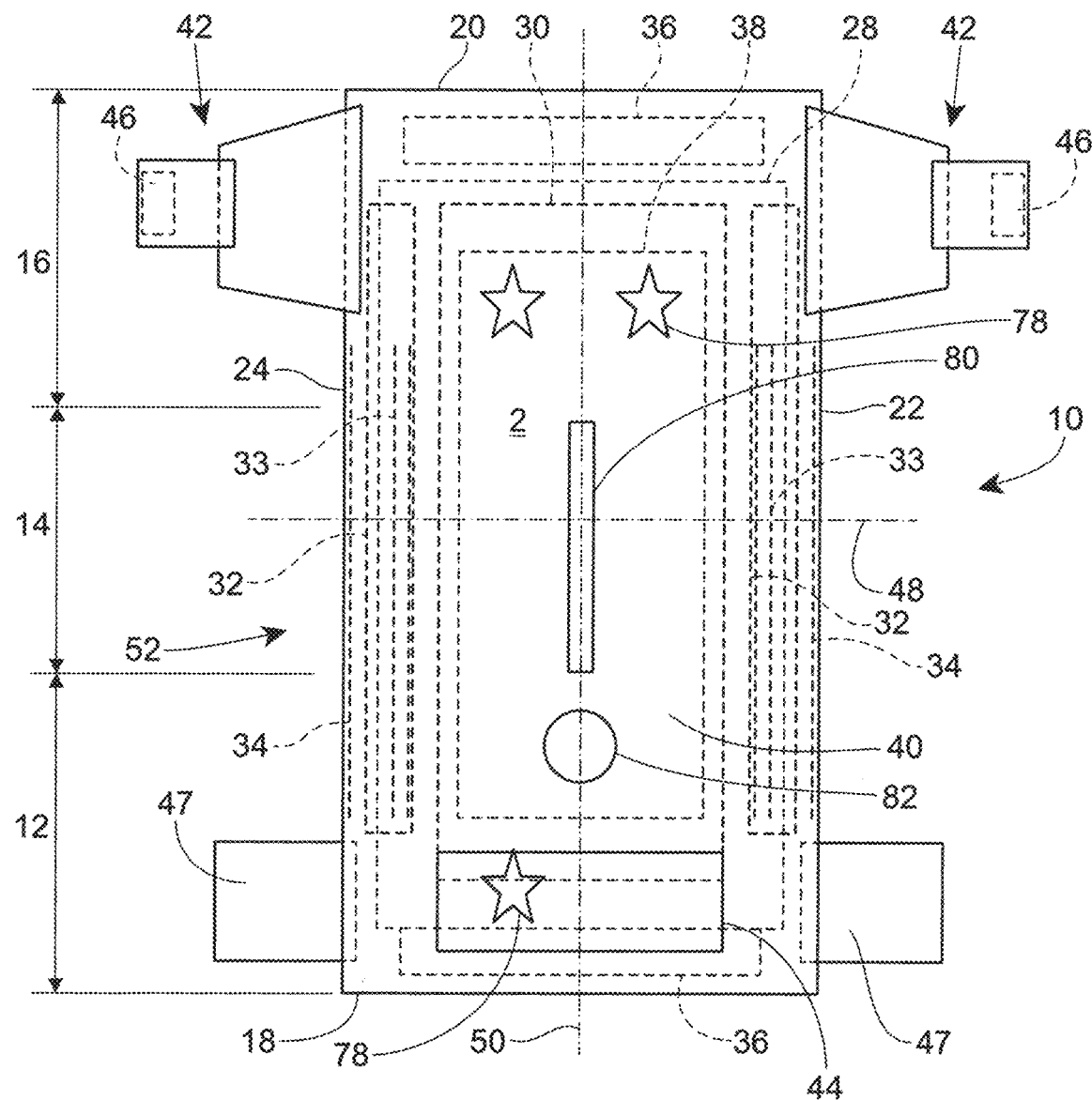
FIG. 1 is a plan view of an example absorbent article in the form of a taped diaper, garment-facing surface facing the viewer, in a flat laid-out state.
Figure 2:
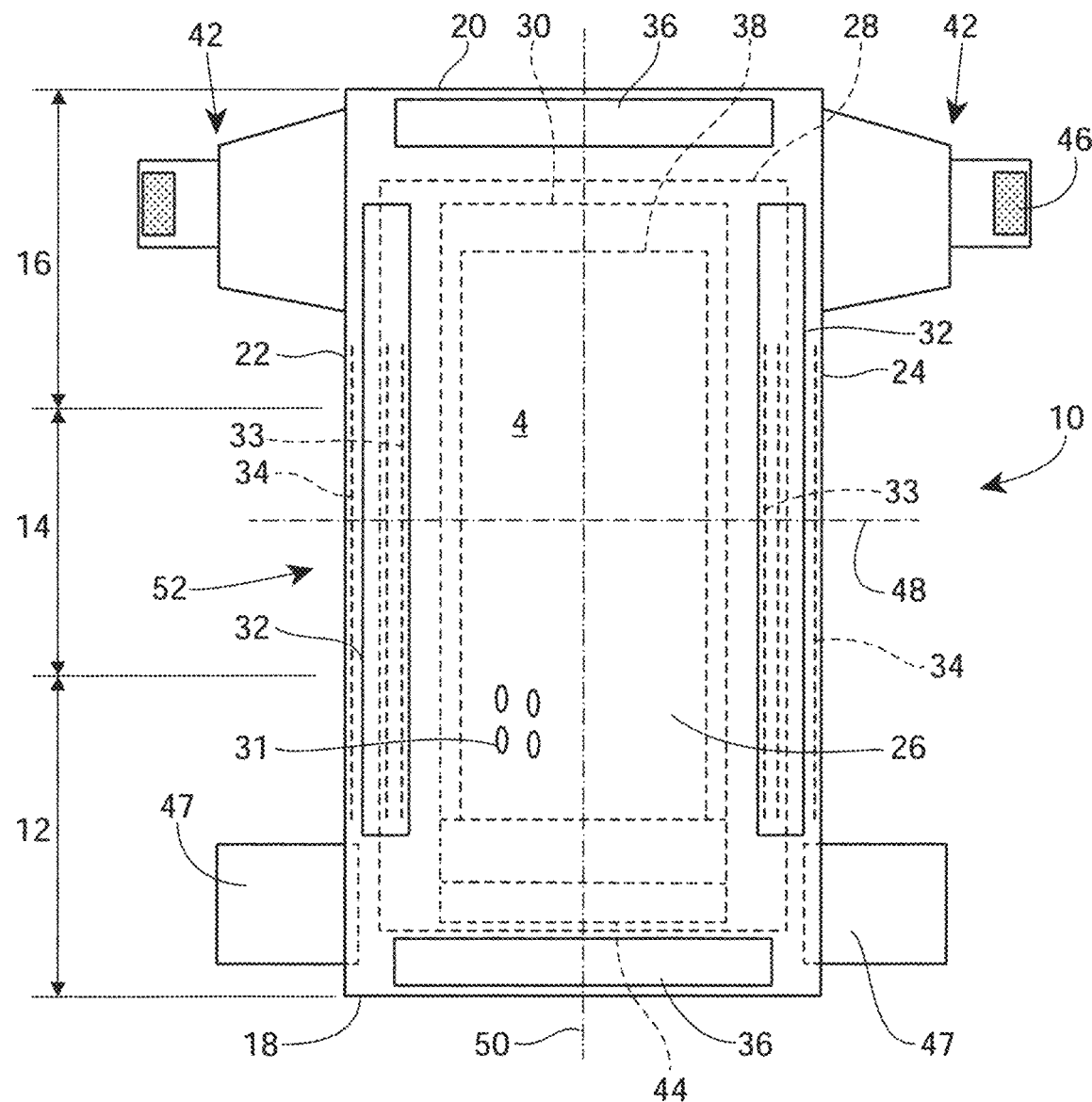
FIG. 2 is a plan view of the example absorbent article of FIG. 1, wearer-facing surface facing the viewer, in a flat laid-out state.
Figure 3:
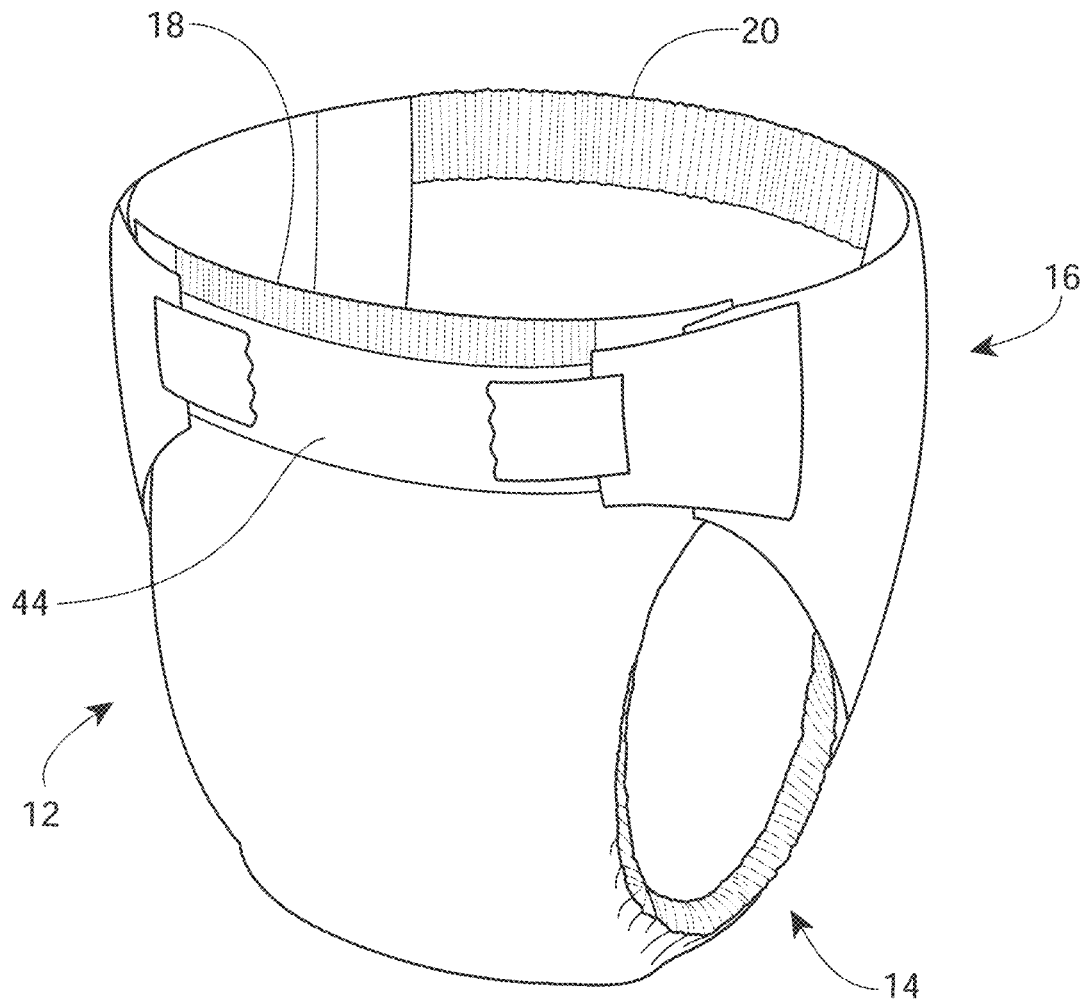
FIG. 3 is a front perspective view of the absorbent article of FIGS. 1 and 2 in a fastened position.

An example absorbent article 10 according to the present disclosure, shown in the form of a taped diaper, is represented in FIGS. 1-3. FIG. 1 is a plan view of the example absorbent article 10, garment-facing surface 2 facing the viewer in a flat, laid-out state (i.e., no elastic contraction). FIG. 2 is a plan view of the example absorbent article 10 of FIG. 1, wearer-facing surface 4 facing the viewer in a flat, laid-out state. FIG. 3 is a front perspective view of the absorbent article 10 of FIGS. 1 and 2 in a fastened configuration. The absorbent article 10 of FIGS. 1-3 is shown for illustration purposes only as the present disclosure may be used for making a wide variety of diapers, including adult incontinence products, pants, or other absorbent articles, such as sanitary napkins and absorbent pads, for example.

The absorbent article 10 may comprise a front waist region 12, a crotch region 14, and a back waist region 16. The crotch region 14 may extend intermediate the front waist region 12 and the back waist region 16. The front wait region 12, the crotch region 14, and the back waist region 16 may each be ⅓ of the length of the absorbent article 10. The absorbent article 10 may comprise a front end edge 18, a back end edge 20 opposite to the front end edge 18, and longitudinally extending, transversely opposed side edges 22 and 24 defined by the chassis 52.

The absorbent article 10 may comprise a liquid permeable topsheet 26, a liquid impermeable backsheet 28, and an absorbent core 30 positioned at least partially intermediate the topsheet 26 and the backsheet 28. The absorbent article 10 may also comprise one or more pairs of barrier leg cuffs 32 with or without elastics 33, one or more pairs of leg elastics 34, one or more elastic waistbands 36, and/or one or more acquisition materials 38. The acquisition material or materials 38 may be positioned intermediate the topsheet 26 and the absorbent core 30. An outer cover nonwoven material 40, such as a nonwoven web, may cover a garment-facing side of the backsheet 28. The absorbent article 10 may comprise back ears 42 in the back waist region 16. The back ears 42 may comprise fasteners 46 and may extend from the back waist region 16 of the absorbent article 10 and attach (using the fasteners 46) to the landing zone area or landing zone material 44 on a garment-facing portion of the front waist region 12 of the absorbent article 10. The absorbent article 10 may also have front ears 47 in the front waist region 12. Instead of two front ears 47, the absorbent article 10 may have a single piece front belt that may function as a landing zone as well. The absorbent article 10 may have a central lateral (or transverse) axis 48 and a central longitudinal axis 50. The central lateral axis 48 extends perpendicular to the central longitudinal axis 50.

Figure 4:
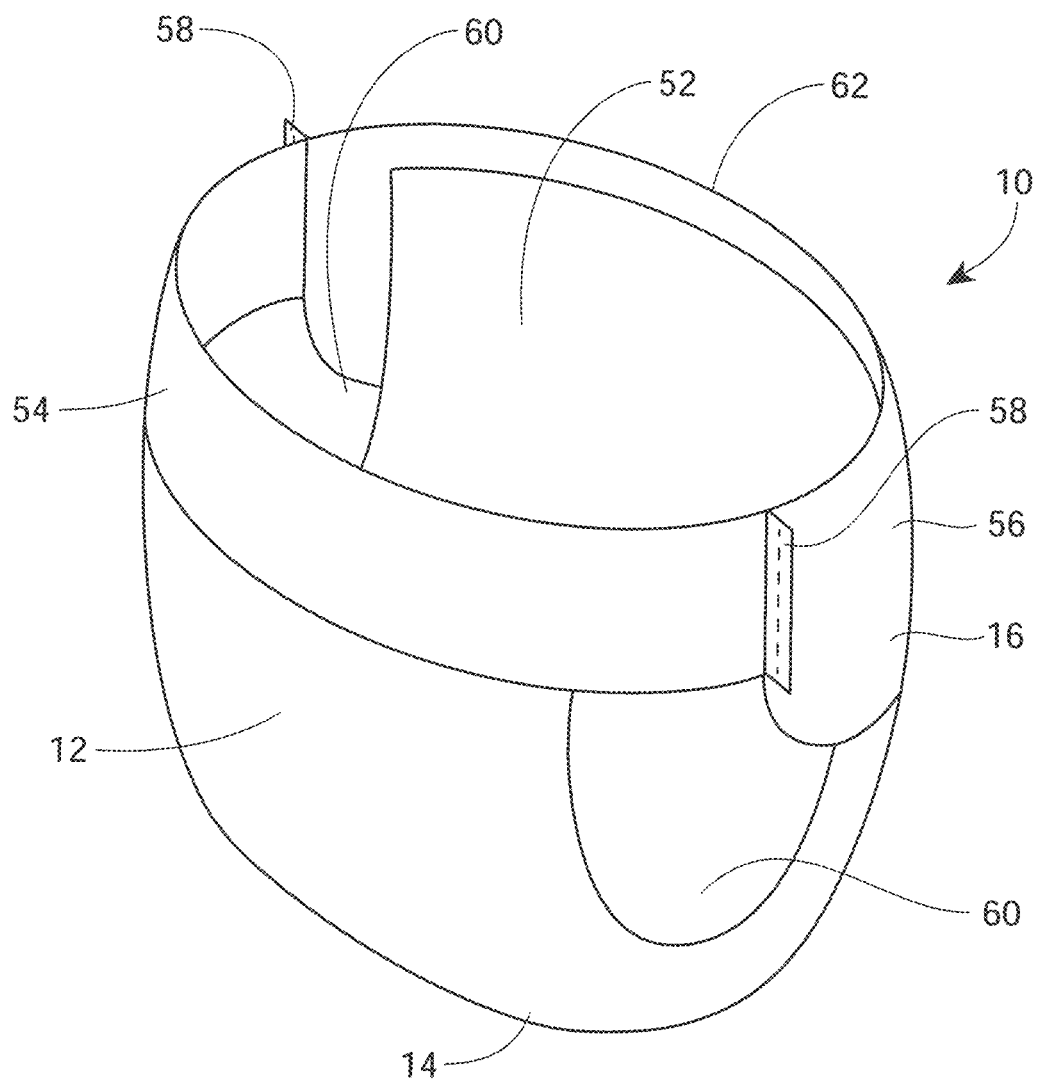
FIG. 4 is a front perspective view of an absorbent article in the form of a pant.
Figure 5:
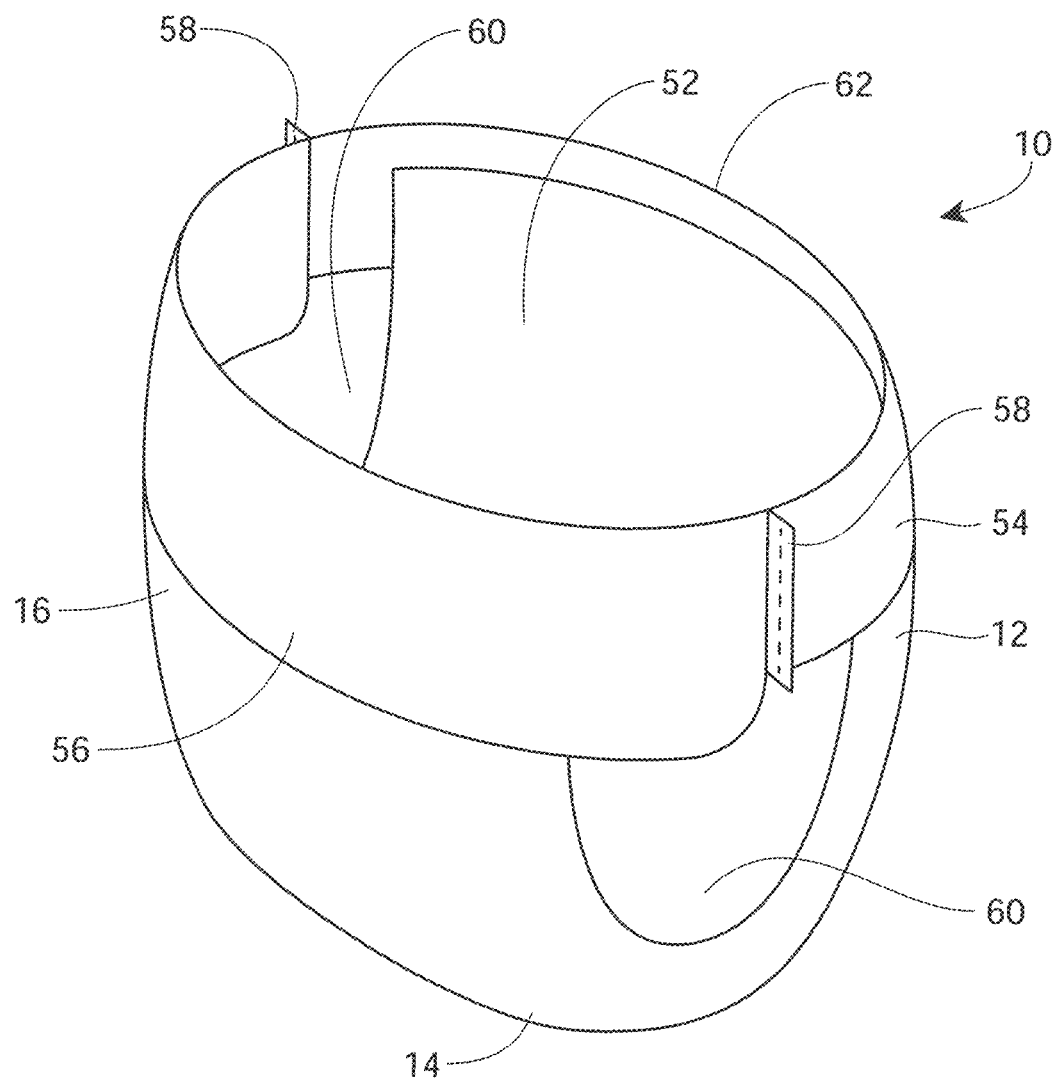
FIG. 5 is a rear perspective view of the absorbent article of FIG. 4.
Figure 6:
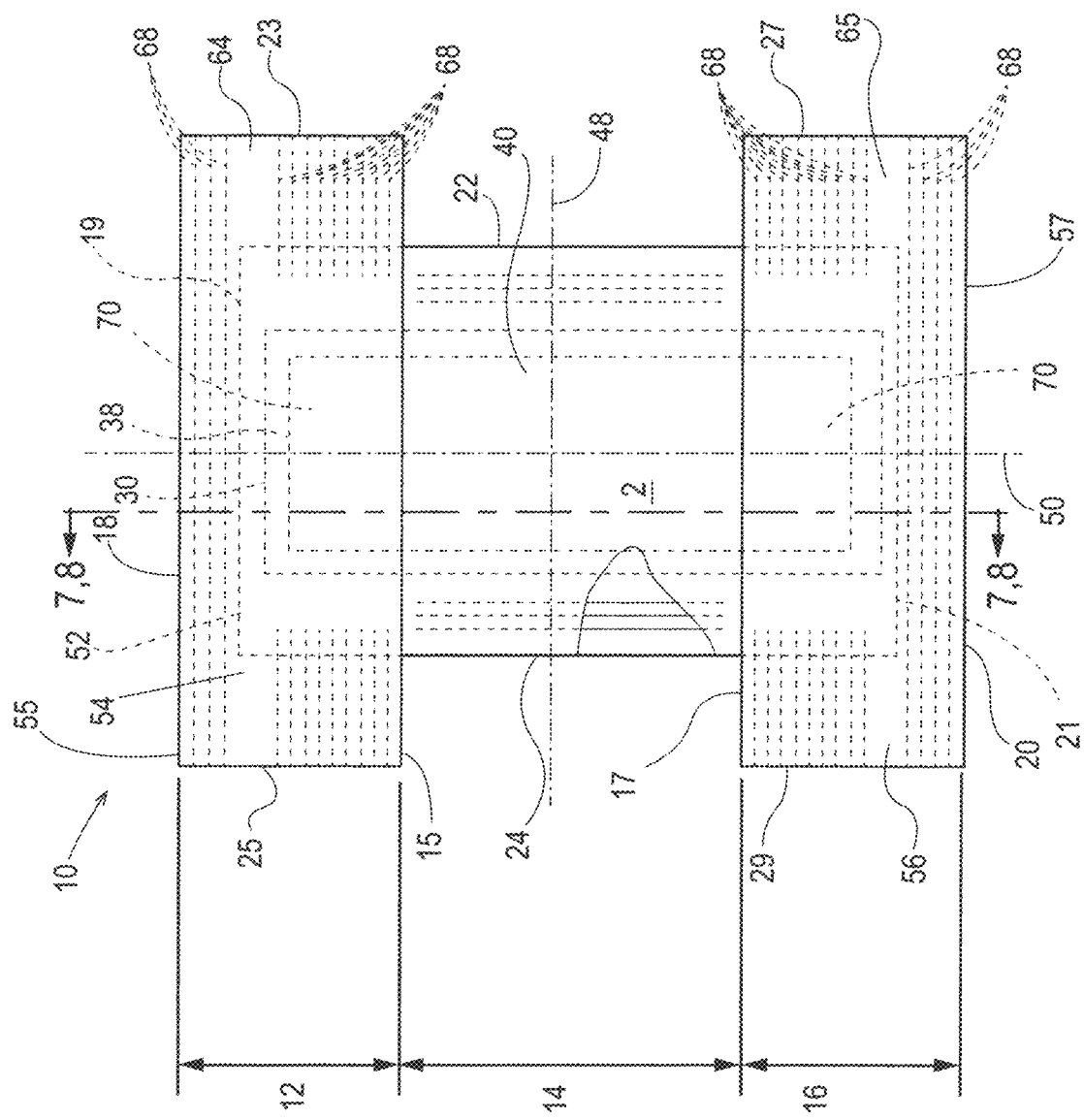
FIG. 6 is a plan view of the absorbent article of FIG. 4, laid flat, with a garment-facing surface facing the viewer.
Figure 7:
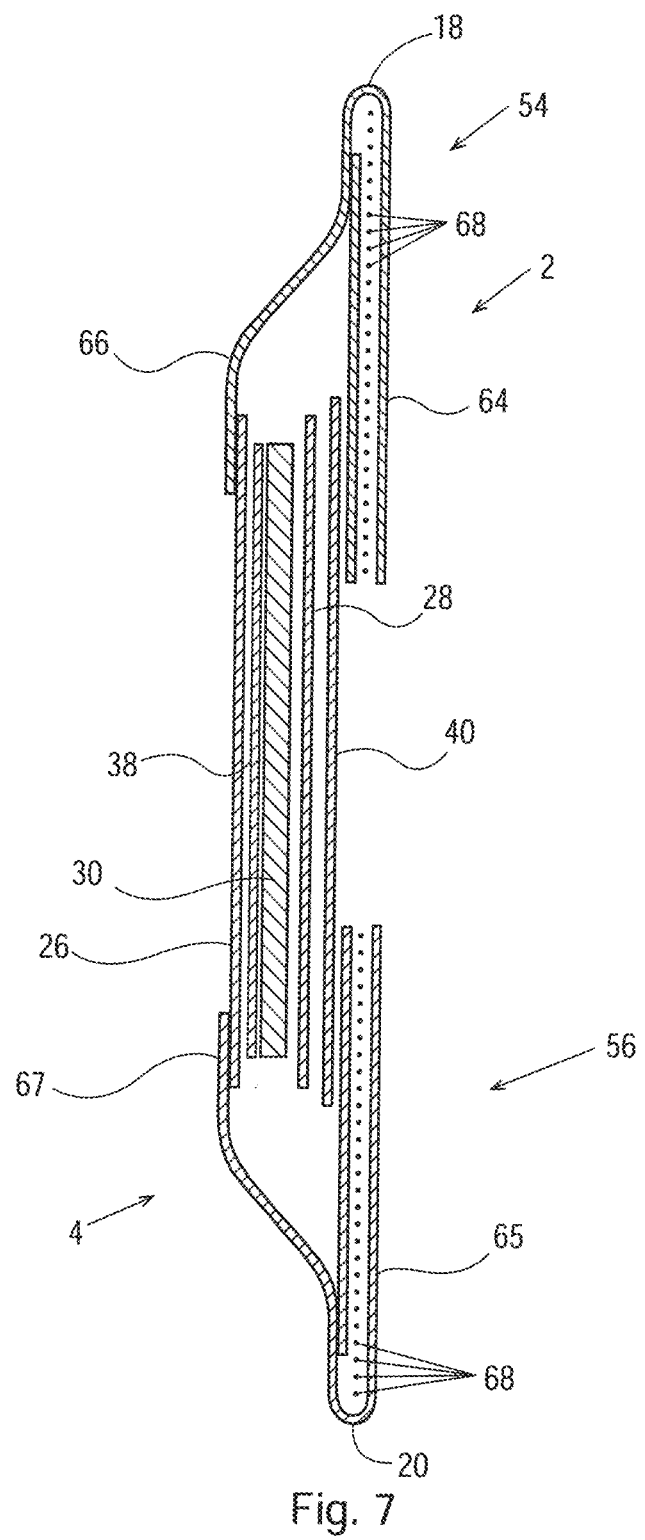
FIG. 7 is a cross-sectional view of the absorbent article taken about line 7-7 of FIG. 6.
Figure 8:
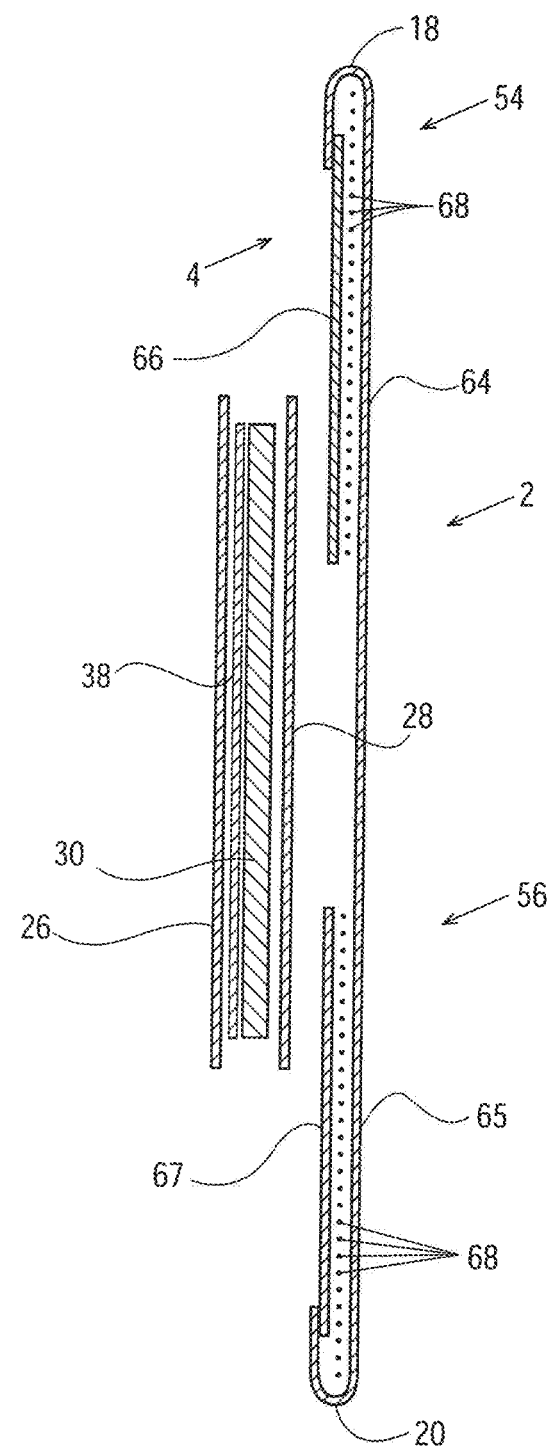
FIG. 8 is a cross-sectional view of the absorbent article taken about line 8-8 of FIG. 6.

In other instances, the absorbent article may be in the form of a pant having permanent or refastenable side seams. Suitable refastenable seams are disclosed in U.S. Pat. Appl. Pub. No. 2014/0005020 and U.S. Pat. No. 9,421,137. Referring to FIGS. 4-8, an example absorbent article 10 in the form of a pant is illustrated. FIG. 4 is a front perspective view of the absorbent article 10. FIG. 5 is a rear perspective view of the absorbent article 10. FIG. 6 is a plan view of the absorbent article 10, laid flat, with the garment-facing surface facing the viewer. Elements of FIG. 4-8 having the same reference number as described above with respect to FIGS. 1-3 may be the same element (e.g., absorbent core 30). FIG. 7 is an example cross-sectional view of the absorbent article taken about line 7-7 of FIG. 6. FIG. 8 is an example cross-sectional view of the absorbent article taken about line 8-8 of FIG. 6. FIGS. 7 and 8 illustrate example forms of front and back belts 54, 56. The absorbent article 10 may have a front waist region 12, a crotch region 14, and a back waist region 16. Each of the regions 12, 14, and 16 may be ⅓ of the length of the absorbent article 10. The absorbent article 10 may have a chassis 52 (sometimes referred to as a central chassis or central panel) comprising a topsheet 26, a backsheet 28, and an absorbent core 30 disposed at least partially intermediate the topsheet 26 and the backsheet 28, and an optional acquisition material 38, similar to that as described above with respect to FIGS. 1-3. The absorbent article 10 may comprise a front belt 54 in the front waist region 12 and a back belt 56 in the back waist region 16. The chassis 52 may be joined to a wearer-facing surface 4 of the front and back belts 54, 56 or to a garment-facing surface 2 of the belts 54, 56. Side edges 23 and 25 of the front belt 54 may be joined to side edges 27 and 29, respectively, of the back belt 56 to form two side seams 58. The side seams 58 may be any suitable seams known to those of skill in the art, such as butt seams or overlap seams, for example. When the side seams 58 are permanently formed or refastenably closed, the absorbent article 10 in the form of a pant has two leg openings 60 and a waist opening circumference 62. The side seams 58 may be permanently joined using adhesives or bonds, for example, or may be refastenably closed using hook and loop fasteners, for example.

Belts

Referring to FIGS. 7 and 8, the front and back belts 54 and 56 may comprise front and back inner belt layers 66 and 67 and front and back outer belt layers 64 and 65 having an elastomeric material (e.g., strands 68 or a film (which may be apertured)) disposed at least partially therebetween. The elastic elements 68 or the film may be relaxed (including being cut) to reduce elastic strain over the absorbent core 30 or, may alternatively, run continuously across the absorbent core 30. The elastics elements 68 may have uniform or variable spacing therebetween in any portion of the belts. The elastic elements 68 may also be pre-strained the same amount or different amounts. The front and/or back belts 54 and 56 may have one or more elastic element free zones 70 where the chassis 52 overlaps the belts 54, 56. In other instances, at least some of the elastic elements 68 may extend continuously across the chassis 52.

The front and back inner belt layers 66, 67 and the front and back outer belt layers 64, 65 may be joined using adhesives, heat bonds, pressure bonds or thermoplastic bonds. Various suitable belt layer configurations can be found in U.S. Pat. Appl. Pub. No. 2013/0211363.

Front and back belt end edges 55 and 57 may extend longitudinally beyond the front and back chassis end edges 19 and 21 (as shown in FIG. 6) or they may be co-terminus. The front and back belt side edges 23, 25, 27, and 29 may extend laterally beyond the chassis side edges 22 and 24. The front and back belts 54 and 56 may be continuous (i.e., having at least one layer that is continuous) from belt side edge to belt side edge (e.g., the transverse distances from 23 to 25 and from 27 to 29). Alternatively, the front and back belts 54 and 56 may be discontinuous from belt side edge to belt side edge (e.g., the transverse distances from 23 to 25 and 27 to 29), such that they are discrete.

As disclosed in U.S. Pat. No. 7,901,393, the longitudinal length (along the central longitudinal axis 50) of the back belt 56 may be greater than the longitudinal length of the front belt 54, and this may be particularly useful for increased buttocks coverage when the back belt 56 has a greater longitudinal length versus the front belt 54 adjacent to or immediately adjacent to the side seams 58.

The front outer belt layer 64 and the back outer belt layer 65 may be separated from each other, such that the layers are discrete or, alternatively, these layers may be continuous, such that a layer runs continuously from the front belt end edge 55 to the back belt end edge 57. This may also be true for the front and back inner belt layers 66 and 67—that is, they may also be longitudinally discrete or continuous. Further, the front and back outer belt layers 64 and 65 may be longitudinally continuous while the front and back inner belt layers 66 and 67 are longitudinally discrete, such that a gap is formed between them—a gap between the front and back inner and outer belt layers 64, 65, 66, and 67 is shown in FIG. 7 and a gap between the front and back inner belt layers 66 and 67 is shown in FIG. 8.

The front and back belts 54 and 56 may include slits, holes, and/or perforations providing increased breathability, softness, and a garment-like texture. Underwear-like appearance can be enhanced by substantially aligning the waist and leg edges at the side seams 58 (see FIGS. 4 and 5).

The front and back belts 54 and 56 may comprise graphics (see e.g., 78 of FIG. 1). The graphics may extend substantially around the entire circumference of the absorbent article 10 and may be disposed across side seams 58 and/or across proximal front and back belt seams 15 and 17; or, alternatively, adjacent to the seams 58, 15, and 17 in the manner described in U.S. Pat. No. 9,498,389 to create a more underwear-like article. The graphics may also be discontinuous.

Alternatively, instead of attaching belts 54 and 56 to the chassis 52 to form a pant, discrete side panels may be attached to side edges of the chassis 22 and 24.

The nonwoven webs with visually discernable patterns may be used as nonwoven components of the belts, or portions thereof.

Topsheet

The topsheet 26 is the part of the absorbent article 10 that is in contact with the wearer's skin. The topsheet 26 may be joined to portions of the backsheet 28, the absorbent core 30, the barrier leg cuffs 32, and/or any other layers as is known to those of ordinary skill in the art. The topsheet 26 may be compliant, soft-feeling, and non-irritating to the wearer's skin. Further, at least a portion of, or all of, the topsheet may be liquid permeable, permitting liquid bodily exudates to readily penetrate through its thickness. A suitable topsheet may be manufactured from a wide range of materials, such as porous foams, reticulated foams, apertured plastic films, woven materials, nonwoven webs, woven or nonwoven webs of natural fibers (e.g., wood or cotton fibers), synthetic fibers or filaments (e.g., polyester or polypropylene or bicomponent PE/PP fibers or mixtures thereof), or a combination of natural and synthetic fibers. The topsheet may have one or more layers. The topsheet may be apertured (FIG. 2, element 31), may have any suitable three-dimensional features, and/or may have a plurality of embossments (e.g., a bond pattern). The topsheet may be apertured by overbonding a material and then rupturing the overbonds through ring rolling, such as disclosed in U.S. Pat. No. 5,628,097, to Benson et al., issued on May 13, 1997 and disclosed in U.S. Pat. Appl. Publication No. US 2016/0136014 to Arora et al. Any portion of the topsheet may be coated with a skin care composition, an antibacterial agent, a surfactant, and/or other beneficial agents. The topsheet may be hydrophilic or hydrophobic or may have hydrophilic and/or hydrophobic portions or layers. If the topsheet is hydrophobic, typically apertures will be present so that bodily exudates may pass through the topsheet.

The nonwoven webs with visually discernable patterns may be used as nonwoven topsheets, or portions thereof.

Backsheet

The backsheet 28 is generally that portion of the absorbent article 10 positioned proximate to the garment-facing surface of the absorbent core 30. The backsheet 28 may be joined to portions of the topsheet 26, the outer cover nonwoven material 40, the absorbent core 30, and/or any other layers of the absorbent article by any attachment methods known to those of skill in the art. The backsheet 28 prevents, or at least inhibits, the bodily exudates absorbed and contained in the absorbent core 10 from soiling articles such as bedsheets, undergarments, and/or clothing. The backsheet is typically liquid impermeable, or at least substantially liquid impermeable. The backsheet may, for example, be or comprise a thin plastic film, such as a thermoplastic film having a thickness of about 0.012 mm to about 0.051 mm. Other suitable backsheet materials may include breathable materials which permit vapors to escape from the absorbent article, while still preventing, or at least inhibiting, bodily exudates from passing through the backsheet.

Outer Cover Nonwoven Material

The outer cover nonwoven material (sometimes referred to as a backsheet nonwoven) 40 may comprise one or more nonwoven materials joined to the backsheet 28 and that covers the backsheet 28. The outer cover nonwoven material 40 forms at least a portion of the garment-facing surface 2 of the absorbent article 10 and effectively "covers" the backsheet 28 so that film is not present on the garment-facing surface 2. The nonwoven webs with visually discernable patterns may be used as the outer cover nonwoven material, or portions thereof.

Absorbent Core

Figure 9:
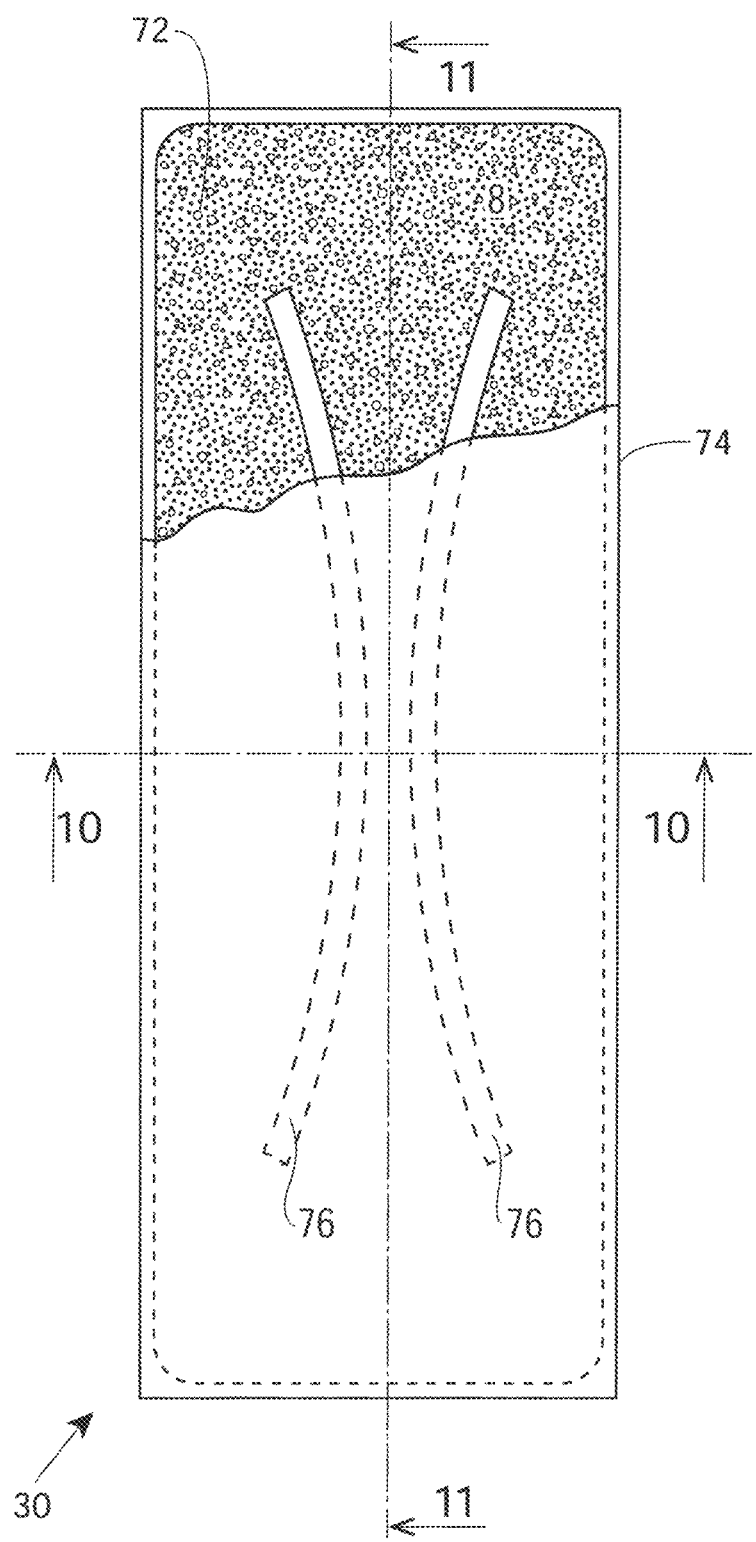
FIG. 9 is a plan view of an example absorbent core or an absorbent article.
Figures 10, 11:
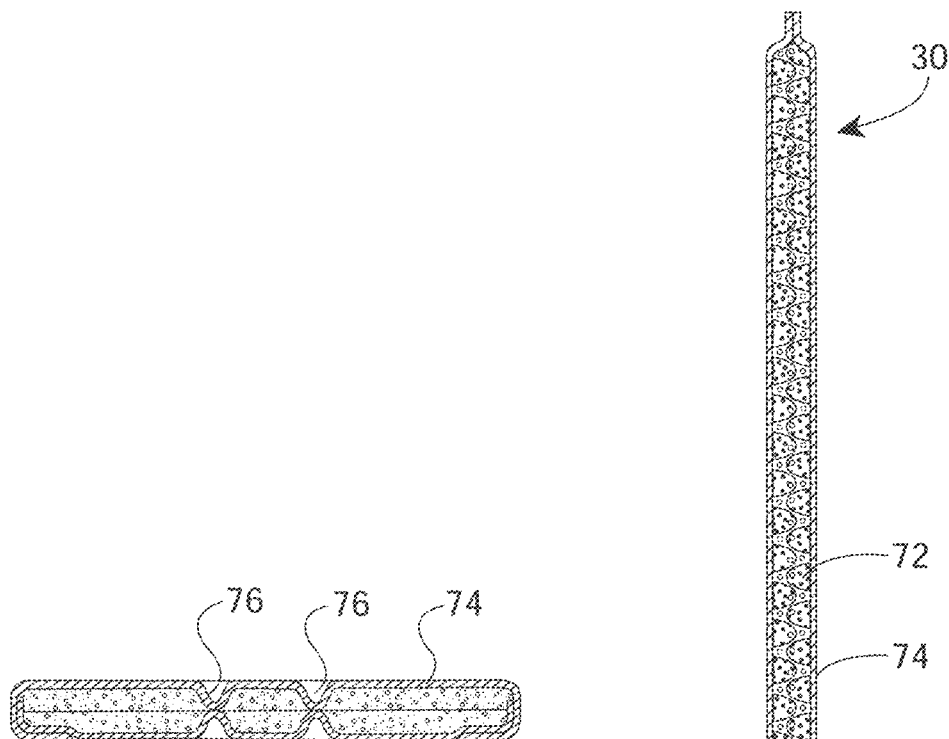
FIG. 10 is a cross-sectional view, taken about line 10-10, of the absorbent core of FIG. 9.
FIG. 11 is a cross-sectional view, taken about line 11-11, of the absorbent core of FIG. 10.

As used herein, the term "absorbent core" 30 refers to the component of the absorbent article 10 having the most absorbent capacity and that comprises an absorbent material. Referring to FIGS. 9-11, in some instances, absorbent material 72 may be positioned within a core bag or a core wrap 74. The absorbent material may be profiled or not profiled, depending on the specific absorbent article. The absorbent core 30 may comprise, consist essentially of, or consist of, a core wrap, absorbent material 72, and glue enclosed within the core wrap. The absorbent material may comprise superabsorbent polymers, a mixture of superabsorbent polymers and air felt, only air felt, and/or a high internal phase emulsion foam. In some instances, the absorbent material may comprise at least 80%, at least 85%, at least 90%, at least 95%, at least 99%, or up to 100% superabsorbent polymers, by weight of the absorbent material. In such instances, the absorbent material may be free of air felt, or at least mostly free of air felt. The absorbent core periphery, which may be the periphery of the core wrap, may define any suitable shape, such as rectangular "T," "Y," "hour-glass," or "dog-bone" shaped, for example. An absorbent core periphery having a generally "dog bone" or "hour-glass" shape may taper along its width towards the crotch region 14 of the absorbent article 10.

Referring to FIGS. 9-11, the absorbent core 30 may have areas having little or no absorbent material 72, where a wearer-facing surface of the core bag 74 may be joined to a garment-facing surface of the core bag 74. These areas having little or no absorbent material and may be referred to as "channels" 76. These channels can embody any suitable shapes and any suitable number of channels may be provided. In other instances, the absorbent core may be embossed to create the impression of channels. The absorbent core in FIGS. 9-11 is merely an example absorbent core. Many other absorbent cores with or without channels are also within the scope of the present disclosure.

Barrier Leg Cuffs/Leg Elastics

Referring to FIGS. 1 and 2, for example, the absorbent article 10 may comprise one or more pairs of barrier leg cuffs 32 and one or more pairs of leg elastics 34. The barrier leg cuffs 32 may be positioned laterally inboard of leg elastics 34. Each barrier leg cuff 32 may be formed by a piece of material which is bonded to the absorbent article 10 so it can extend upwards from a wearer-facing surface 4 of the absorbent article 10 and provide improved containment of body exudates approximately at the junction of the torso and legs of the wearer. The barrier leg cuffs 32 are delimited by a proximal edge joined directly or indirectly to the topsheet and/or the backsheet and a free terminal edge, which is intended to contact and form a seal with the wearer's skin. The barrier leg cuffs 32 may extend at least partially between the front end edge 18 and the back end edge 20 of the absorbent article 10 on opposite sides of the central longitudinal axis 50 and may be at least present in the crotch region 14. The barrier leg cuffs 32 may each comprise one or more elastics 33 (e.g., elastic strands or strips) near or at the free terminal edge. These elastics 33 cause the barrier leg cuffs 32 to help form a seal around the legs and torso of a wearer. The leg elastics 34 extend at least partially between the front end edge 18 and the back end edge 20. The leg elastics 34 essentially cause portions of the absorbent article 10 proximate to the chassis side edges 22, 24 to help form a seal around the legs of the wearer. The leg elastics 34 may extend at least within the crotch region 14.

The nonwoven webs with visually discernable patterns may be used as nonwoven components of the barrier leg cuffs, or portions thereof.

Waistband

Referring to FIGS. 1 and 2, the absorbent article 10 may comprise one or more elastic waistbands 36 or non-elastic waistband. The elastic waistbands 36 may be positioned on the garment-facing surface 2 or the wearer-facing surface 4. As an example, a first elastic waistband 36 may be present in the front waist region 12 near the front belt end edge 18 and a second elastic waistband 36 may be present in the back waist region 16 near the back end edge 20. The elastic waistbands 36 may aid in sealing the absorbent article 10 around a waist of a wearer and at least inhibiting bodily exudates from escaping the absorbent article 10 through the waist opening circumference. In some instances, an elastic waistband may fully surround the waist opening circumference of an absorbent article.

The nonwoven webs with visually discernable patterns may be used as nonwoven components of the waistband, or portions thereof.

Acquisition Materials

Referring to FIGS. 1, 2, 7, and 8, one or more acquisition materials 38 may be present at least partially intermediate the topsheet 26 and the absorbent core 30. The acquisition materials 38 are typically hydrophilic materials that provide significant wicking of bodily exudates. These materials may dewater the topsheet 26 and quickly move bodily exudates into the absorbent core 30. The acquisition materials 38 may comprise one or more nonwoven webs, foams, cellulosic materials, cross-linked cellulosic materials, air laid cellulosic nonwoven webs, spunlace materials, or combinations thereof, for example. In some instances, portions of the acquisition materials 38 may extend through portions of the topsheet 26, portions of the topsheet 26 may extend through portions of the acquisition materials 38, and/or the topsheet 26 may be nested with the acquisition materials 38. Typically, an acquisition material 38 may have a width and length that are smaller than the width and length of the topsheet 26. The acquisition material may be a secondary topsheet in the feminine pad context. The acquisition material may have one or more channels as described above with reference to the absorbent core 30 (including the embossed version). The channels in the acquisition material may align or not align with channels in the absorbent core 30. In an example, a first acquisition material may comprise a nonwoven web and as second acquisition material may comprise a cross-linked cellulosic material. The nonwoven webs with visually discernable patterns may be used as nonwoven components of the acquisition materials, or portions thereof.

Landing Zone

Referring to FIGS. 1 and 2, the absorbent article 10 may have a landing zone area 44 that is formed in a portion of the garment-facing surface 2 of the outer cover nonwoven material 40. The landing zone area 44 may be in the back waist region 16 if the absorbent article 10 fastens from front to back or may be in the front waist region 12 if the absorbent article 10 fastens back to front. In some instances, the landing zone 44 may be or may comprise one or more discrete nonwoven materials that are attached to a portion of the outer cover nonwoven material 40 in the front waist region 12 or the back waist region 16 depending upon whether the absorbent article fastens in the front or the back. In essence, the landing zone 44 is configured to receive the fasteners 46 and may comprise, for example, a plurality of loops configured to be engaged with, a plurality of hooks on the fasteners 46, or vice versa.

The nonwoven webs with visually discernable patterns may be used as nonwoven components of the landing zone, or portions thereof.

Wetness Indicator/Graphics

Referring to FIG. 1, the absorbent articles 10 of the present disclosure may comprise graphics 78 and/or wetness indicators 80 that are visible from the garment-facing surface 2. The graphics 78 may be printed on the landing zone 40, the backsheet 28, and/or at other locations. The wetness indicators 80 are typically applied to the absorbent core facing side of the backsheet 28, so that they can be contacted by bodily exudates within the absorbent core 30. In some instances, the wetness indicators 80 may form portions of the graphics 78. For example, a wetness indicator may appear or disappear and create/remove a character within some graphics. In other instances, the wetness indicators 80 may coordinate (e.g., same design, same pattern, same color) or not coordinate with the graphics 78.

Front and Back Ears

Referring to FIGS. 1 and 2, as referenced above, the absorbent article 10 may have front and/or back ears 47, 42 in a taped diaper context. Only one set of ears may be required in most taped diapers. The single set of ears may comprise fasteners 46 configured to engage the landing zone or landing zone area 44. If two sets of ears are provided, in most instances, only one set of the ears may have fasteners 46, with the other set being free of fasteners. The ears, or portions thereof, may be elastic or may have elastic panels. In an example, an elastic film or elastic strands may be positioned intermediate a first nonwoven web and a second nonwoven web. The elastic film may or may not be apertured. The ears may be shaped. The ears may be integral (e.g., extension of the outer cover nonwoven material 40, the backsheet 28, and/or the topsheet 26) or may be discrete components attached to a chassis 52 of the absorbent article on a wearer-facing surface 4, on the garment-facing surface 2, or intermediate the two surfaces 4, 2.

The nonwoven webs with visually discernable patterns may be used as nonwoven components of the front and back ears, or portions thereof.

Sensors

Referring again to FIG. 1, the absorbent articles of the present disclosure may comprise a sensor system 82 for monitoring changes within the absorbent article 10. The sensor system 82 may be discrete from or integral with the absorbent article 10. The absorbent article 10 may comprise sensors that can sense various aspects of the absorbent article 10 associated with insults of bodily exudates such as urine and/or BM (e.g., the sensor system 82 may sense variations in temperature, humidity, presence of ammonia or urea, various vapor components of the exudates (urine and feces), changes in moisture vapor transmission through the absorbent articles garment-facing layer, changes in translucence of the garment-facing layer, and/or color changes through the garment-facing layer). Additionally, the sensor system 82 may sense components of urine, such as ammonia or urea and/or byproducts resulting from reactions of these components with the absorbent article 10. The sensor system 82 may sense byproducts that are produced when urine mixes with other components of the absorbent article 10 (e.g., adhesives, agm). The components or byproducts being sensed may be present as vapors that may pass through the garment-facing layer. It may also be desirable to place reactants in the absorbent article that change state (e.g. color, temperature) or create a measurable byproduct when mixed with urine or BM. The sensor system 82 may also sense changes in pH, pressure, odor, the presence of gas, blood, a chemical marker or a biological marker or combinations thereof. The sensor system 82 may have a component on or proximate to the absorbent article that transmits a signal to a receiver more distal from the absorbent article, such as an iPhone, for example. The receiver may output a result to communicate to the caregiver a condition of the absorbent article 10. In other instances, a receiver may not be provided, but instead the condition of the absorbent article 10 may be visually or audibly apparent from the sensor on the absorbent article.

Packages

The absorbent articles of the present disclosure may be placed into packages. The packages may comprise nonwoven webs, polymeric films, and/or other materials. Graphics and/or indicia relating to properties of the absorbent articles may be formed on, printed on, positioned on, and/or placed on outer portions of the packages. Each package may comprise a plurality of absorbent articles. The absorbent articles may be packed under compression so as to reduce the size of the packages, while still providing an adequate number of absorbent articles per package. By packaging the absorbent articles under compression, caregivers can easily handle and store the packages, while also providing distribution savings to manufacturers owing to the size of the packages. The nonwoven webs with visually discernable patterns may be used as nonwoven components of the packages, or portions thereof.

Sanitary Napkin

Figure 12:
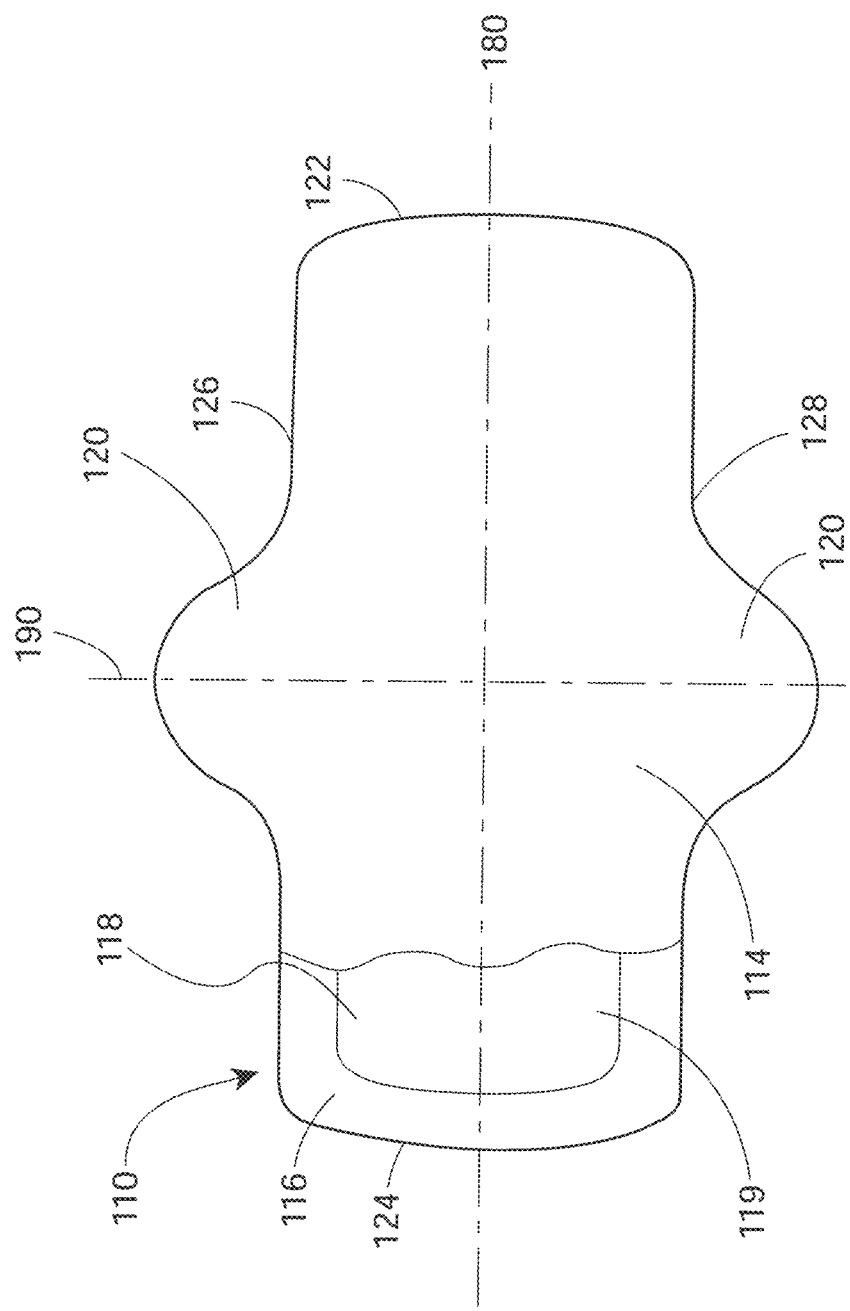
FIG. 12 is a plan view of an example absorbent article of the present disclosure that is a sanitary napkin.

Referring to FIG. 12, an absorbent article of the present disclosure may be a sanitary napkin 110. The sanitary napkin 110 may comprise a liquid permeable topsheet 114, a liquid impermeable, or substantially liquid impermeable, backsheet 116, and an absorbent core 118. The liquid impermeable backsheet 116 may or may not be vapor permeable. The absorbent core 118 may have any or all of the features described herein with respect to the absorbent core 30 and, in some forms, may have a secondary topsheet 119 (STS) instead of the acquisition materials disclosed above. The STS 119 may comprise one or more channels, as described above (including the embossed version). In some forms, channels in the STS 119 may be aligned with channels in the absorbent core 118. The sanitary napkin 110 may also comprise wings 120 extending outwardly with respect to a longitudinal axis 180 of the sanitary napkin 110. The sanitary napkin 110 may also comprise a lateral axis 190. The wings 120 may be joined to the topsheet 114, the backsheet 116, and/or the absorbent core 118. The sanitary napkin 110 may also comprise a front edge 122, a back edge 124 longitudinally opposing the front edge 122, a first side edge 126, and a second side edge 128 longitudinally opposing the first side edge 126. The longitudinal axis 180 may extend from a midpoint of the front edge 122 to a midpoint of the back edge 124. The lateral axis 190 may extend from a midpoint of the first side edge 128 to a midpoint of the second side edge 128. The sanitary napkin 110 may also be provided with additional features commonly found in sanitary napkins as is known in the art.

The nonwoven webs with visually discernable patterns may be used as nonwoven components of sanitary napkins, or portions thereof.

Nonwoven Webs with Visually Discernible Patterns

The nonwoven webs with visually discernable patterns are now discussed. The visually discernable patterns may be formed by three-dimensional features. FIGS. 13-17 illustrate example visually discernable patterns of three-dimensional features for nonwoven webs. Such nonwoven webs may be used as various components of, or portions of components of, absorbent articles, such as topsheets, wings, outer cover nonwoven materials, belts, waistbands, leg cuffs, waist cuffs, landing zones, acquisition materials, and/or ears, for example.

Referring to FIGS. 13-17, the nonwoven webs of the present disclosure may comprise a first surface and a second surface. A visually discernible pattern of three-dimensional features 200 may be present on the first surface and/or the second surface. The visually discernible pattern of three-dimensional features 200 may comprise one or more, or a plurality of, first regions 202 and a plurality of second regions 204. The one or more first regions 202 may be different than then plurality of second regions 204 in a value of average intensive property, such as basis weight, volumetric density, and/or caliper, for example. This difference in the value of average intensive properties will be discussed further below. The one or more first regions 202 may be low basis weight and compressed, thereby resembling stitching of a quilted fabric and the plurality of second regions 204 may be high density, lofty, and soft, thereby resembling pillows of a quilted fabric in between the stitching. As such, the nonwoven webs of the present disclosure provide a quilted fabric appearance and texture, which is highly consumer desirable and attributed to premiumness of the nonwoven webs. This quilted fabric appearance is created through the use varying the intensive properties between the one or more first regions and the plurality of second regions.

Referring again to FIGS. 13-17, the one or more first regions 202 may comprise a first line 206, a second line 208, and a third line 210 extending at least partially, or fully, intermediate the first line 206 and the second line 208 in a direction transverse the first line 206 and the second line 208. The first line 206 may extend in a direction substantially parallel to (+/-0.1 to 5 degrees, for example), or parallel to, the second line 208. The third line 210 may have a positive slope or a negative slope, relative to the first and second lines 206, 208. The first line 206 and the second line 208 may have a first length, and the third line 210 may have a second length. The first length may be greater than the second length. The first line 206 may have a first width, the second line 208 may have a second width, and the third line 210 may have a third width. The first, second, and third widths may be the same, substantially the same, or may be different. In some instances, two of the first, second, and third widths may be the same or different.

The one or more first regions 202 may comprise a fourth line 212 extending at least partially, or fully, intermediate the first line 206 and the second line 208 in a direction transverse to the first line 206 and the second line 208. The fourth line 212 may be the same as or similar to that described herein with respect to the third line 210. The third line 210 and the fourth line 212 may have the same or substantially the same length. The third line 210 and the fourth line 212 may have the same or substantially the same slope, whether the slope is positive or negative. The third line 210 and the fourth line 212 may have the same, substantially the same, or different widths. The one or more first regions 202 may comprise a number of other lines extending at least partially, or fully, intermediate the first line 206 and the second line 208 in a direction transverse to the first line 206 and the second line 208. These other lines may be the same as or similar to that described herein with respect to the third line 210 and the fourth line 212.

The one or more first regions 202 may comprise a fifth line 214 extending in a direction parallel to, or substantially parallel to, the first line 206. The fifth line 214 may be substantially symmetrical to, or symmetrical to, the second line 208, about the first line 206. The one or more first regions 202 may comprise a sixth line 216 extending transversely at least partially intermediate, or fully intermediate, the first line 206 and the fifth line 214. The sixth line 216 may have a positive or a negative slope, relative to the first line 206 and the fifth line 214. The sixth line 216 may be symmetrical to, or substantially symmetrical to, the third line 210 about the first line 206. The one or more first regions 202 may comprise a seventh line 218 extending at least partially, or fully, intermediate the first line 206 and the fifth line 214, in a direction transverse to the first line 206 and the fifth line 214. The seventh line 218 may be the same as or similar to that described herein with respect to the sixth line 216. The sixth line 216 and the seventh line 218 may have the same or substantially the same length. The sixth line 216 and the seventh line 212 may have the same or substantially the same slope, whether the slope is positive or negative. The sixth line 216 and the seventh line 212 may have the same, substantially the same, or different widths. The one or more first regions 202 may comprise a number of other lines extending at least partially, or fully, intermediate the first line 206 and the fifth 214 in a direction transverse to the first line 206 and the fifth line 214. These other lines may be the same as or similar to that described herein with respect to the sixth line 216 and the seventh line 218. As is shown in FIGS. 13-17, the visually discernible patterns of three-dimensional features may also include a plurality of other lines arranged in the same way as that described with respect to the first through seventh lines above.

Any of, or all of, the various lines described herein may be continuous or discontinuous. For example, referring to FIG. 15, the first line 206 may comprise a first plurality of first discontinuous elements 220, the second line 208 may comprise a second plurality of second discontinuous elements 222, and/or the third line 210 may comprise a third plurality of third discontinuous elements 224. In some instances, all of the other lines may also have a plurality of discontinuous elements. In other instances, only some of the lines, for example the third line 210, or portions thereof, may have discontinuous elements, while other lines are continuous (for example, the first and second lines). Any of the lines may have the same widths, substantially the same widths, or different widths.

The term "line", as used herein, includes a straight line, a curvilinear line, a line with one or more curvilinear portions, an arcuate line, a line with one or more arcuate portions, whether the line is discontinuous or continuous.

Any of the plurality of second regions 204 discussed herein may be free of all of the first line 206, the second line 208, the third line 210, the fourth line 212, the fifth line 214, the sixth line 216, the seventh line 218, and any other lines shown or described as part of the present disclosure, including the figures. At least some of the first regions 202 may at least partially, or fully, surround at least some of the plurality of second regions 204. In the claims, the various lines may be referred to as a different number (e.g., the "fourth line") depending on which order the lines are presented for antecedent basis purposes.

Figure 14:
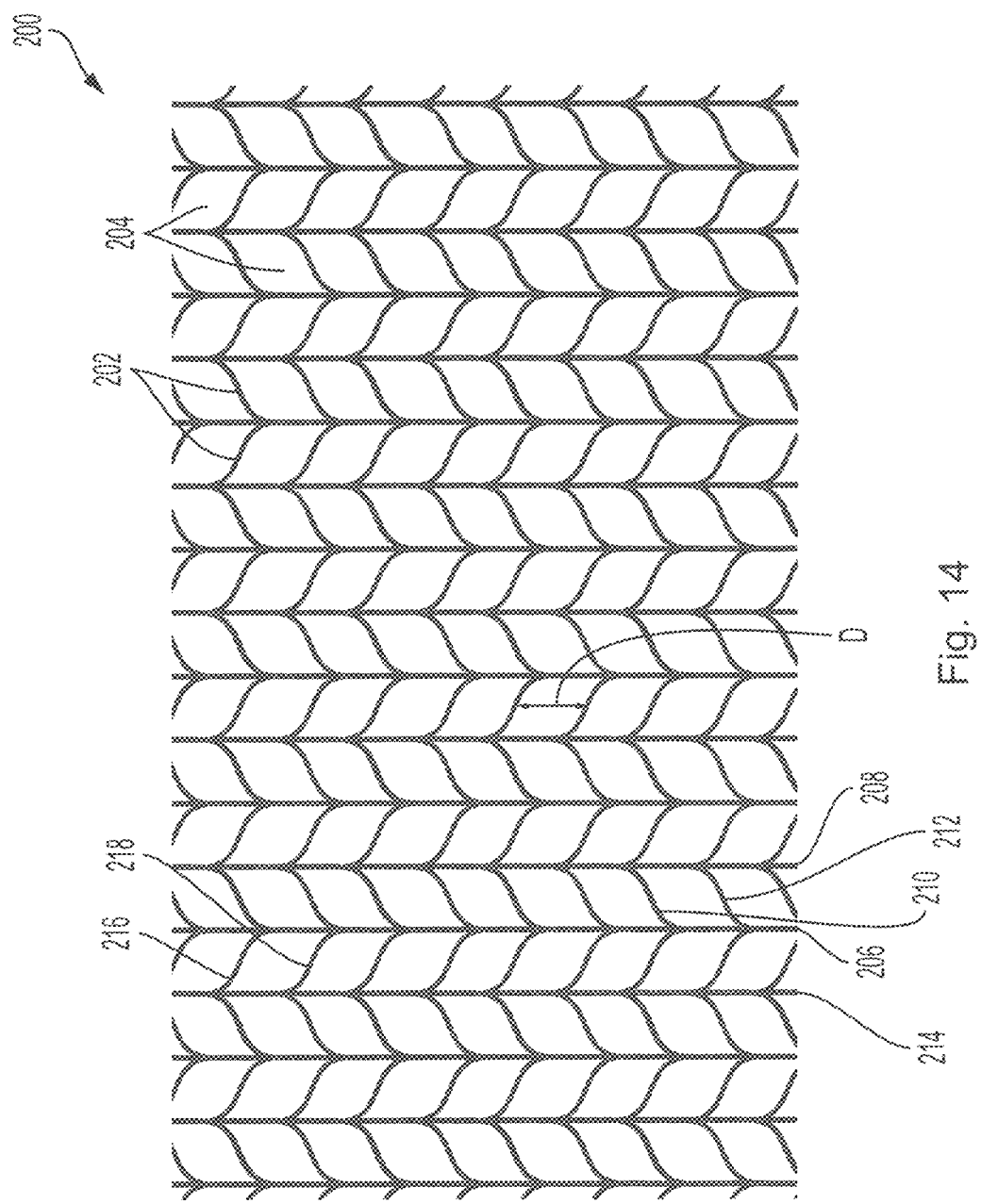

Referring to FIG. 14, the first line 206, the second line 208, and the fifth line 214 may be straight lines, while the third line 210, the fourth line 212, the sixth line 216, and the seventh line 218 may comprise an arcuate portion or a curvilinear line. The curvilinear or arcuate nature of third line 210, the fourth line 212, the sixth line 216, and the seventh line 218 (and other lines in FIG. 14 similar to these lines) may aid the nonwoven web in creating texture and appearance of being like a quilted fabric. A distance, D, in a direction parallel to the first line 206, between the third line 210 and the fourth line 212 (or other similar lines) may be the same or may vary.

Figure 15:
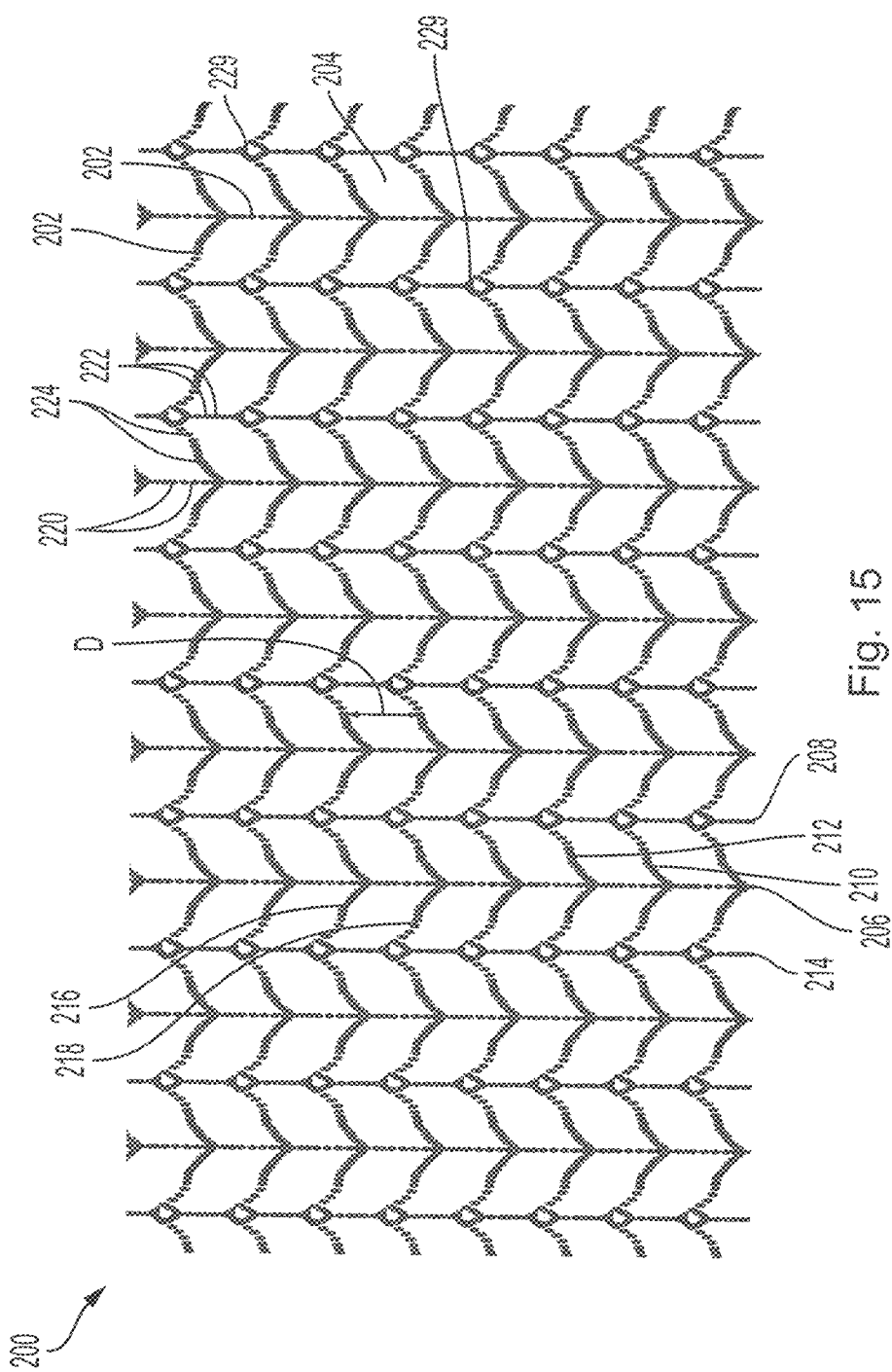

As illustrated in FIG. 15, the first line 206, the second line 208, and the fifth line 214 may be formed of discontinuous elements forming straight lines, while the third line 210, the fourth line 212, the sixth line 216, and the seventh line 218 may be formed of discontinuous elements forming curvilinear lines. The curvilinear or arcuate nature of third line 210, the fourth line 212, the sixth line 216, and the seventh line 218 (and other lines in FIG. 15 similar to these lines) may aid the nonwoven web in creating texture and appearance of being like a quilted fabric. FIG. 15 illustrates a plurality of shapes 229 formed of continuous or discontinuous elements on the first line 206, the second line 208, and the fifth line 214 at the intersections of the first line 206, the second line, 208, and the fifth line 214 with the third line 210, the fourth line 212, the sixth line 216, and the seventh line 218. A distance, D, in a direction parallel to the first line 206, between the third line 210 and the fourth line 212 (or other similar lines) may be the same or may vary.

Figure 13:
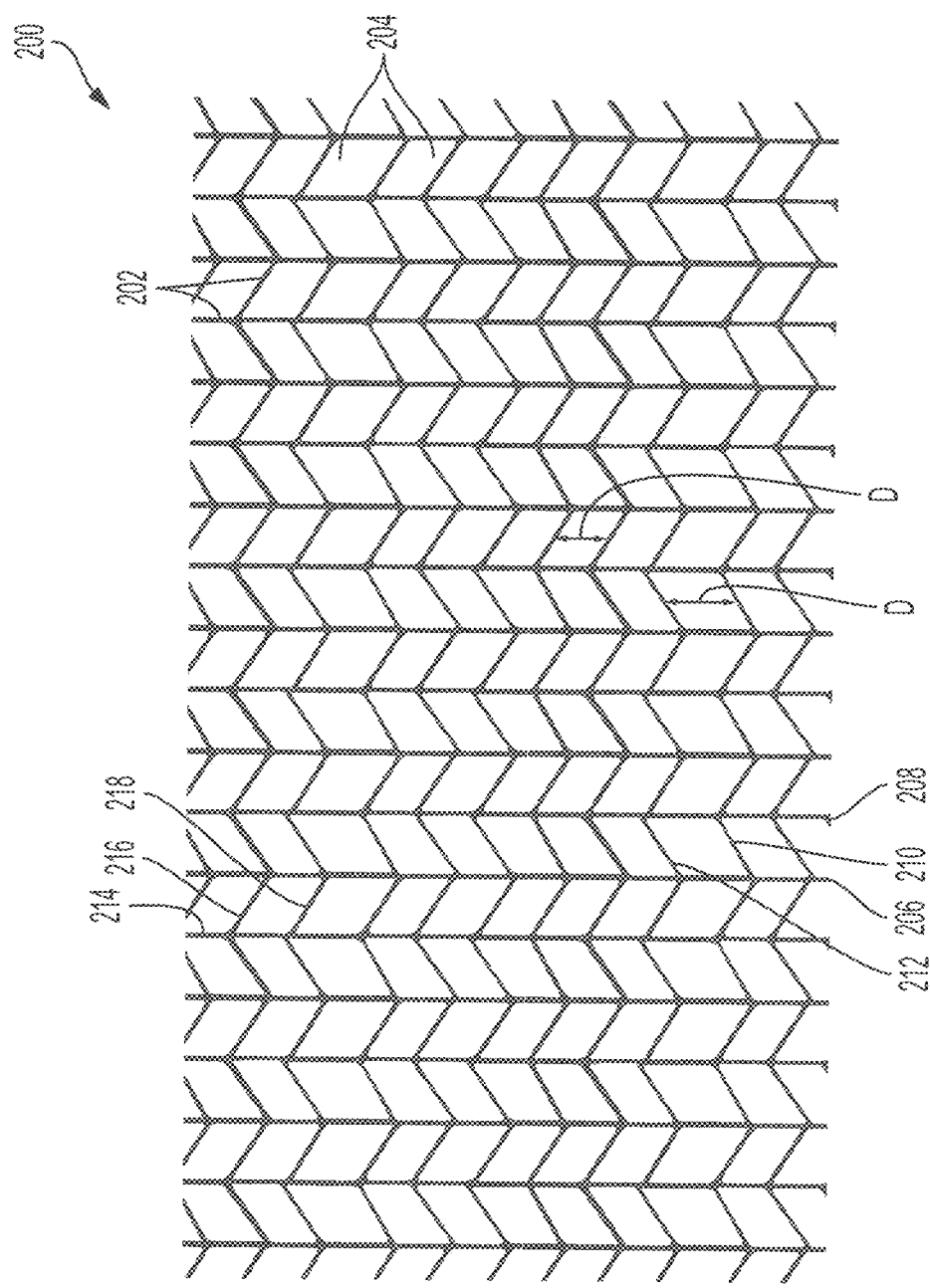
FIGS. 13 to 17 are examples of visually discernable patterns of three-dimensional features for nonwoven webs.
Figure 16:
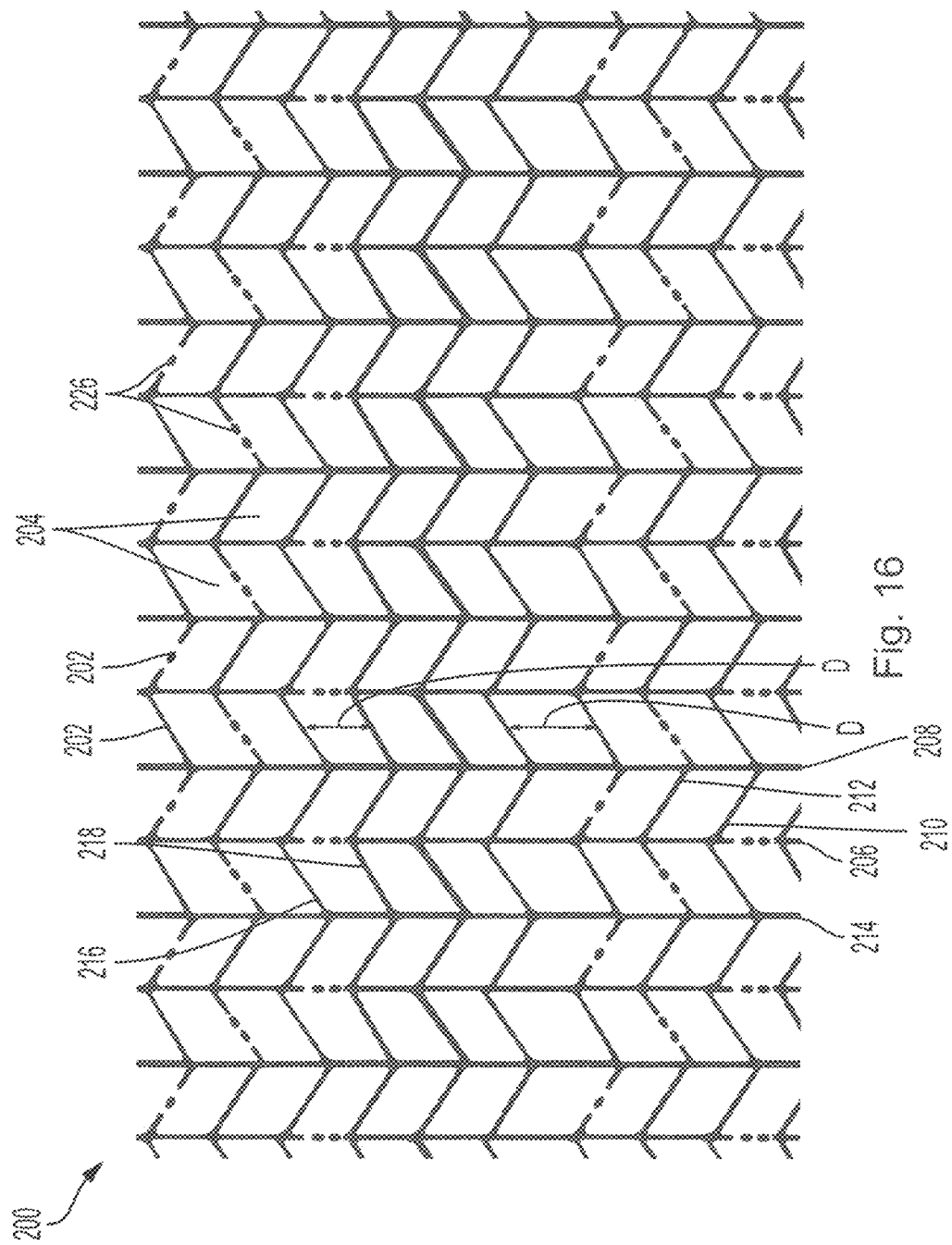

FIG. 16 shows a visually discernible pattern comprising three-dimensional features 200 similar to the visually discernible pattern of FIG. 13, but with occasional discontinuous elements 226 forming portions of some of the lines. It will be understood that other lines or portions thereof may also be discontinuous. A distance, D, in a direction parallel to the first line 206, between the third line 210 and the fourth line 212 (or other similar lines) may be the same or may vary.

Figure 17:
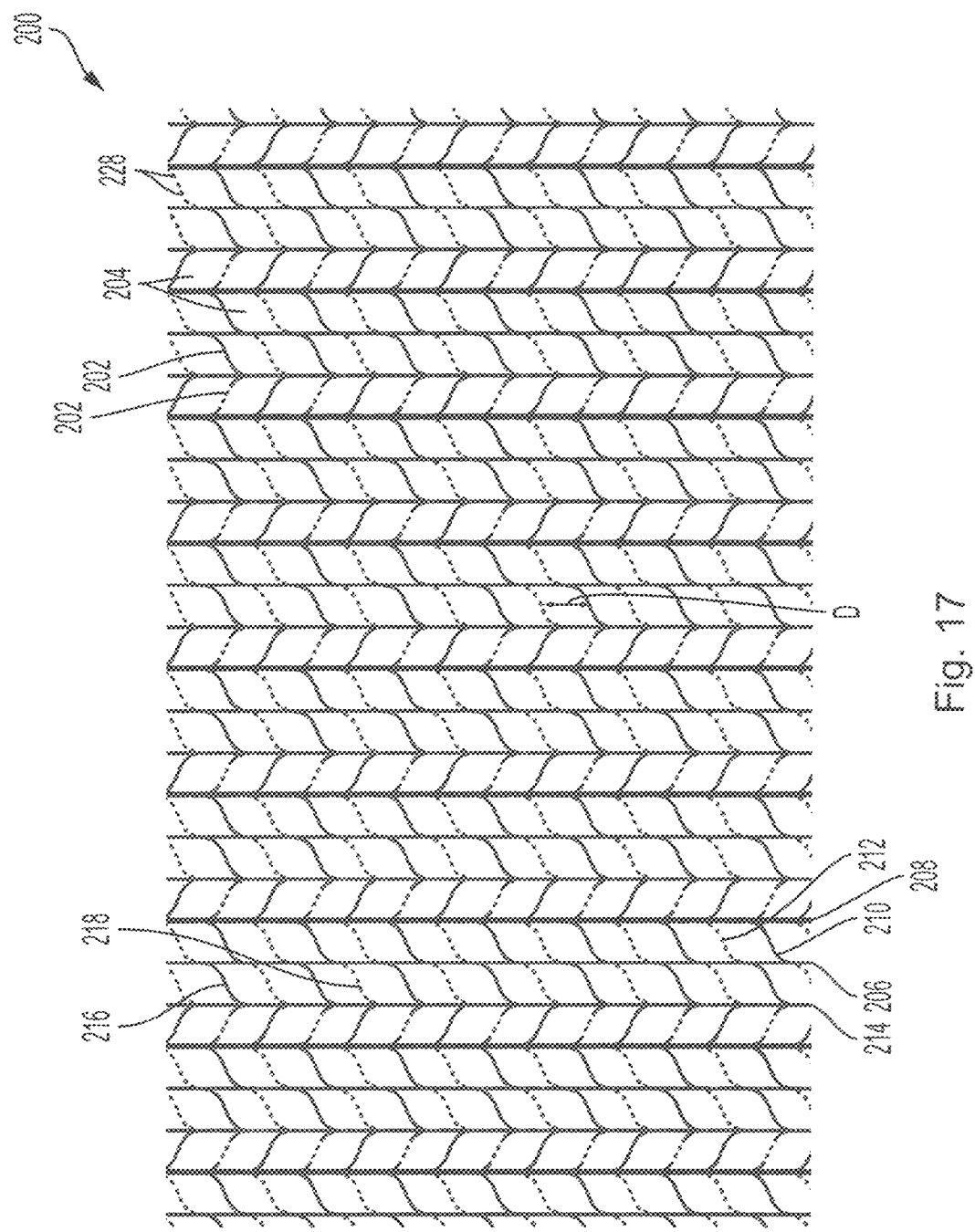

FIG. 17 shows a visually discernible pattern comprising three-dimensional features 200 similar to the visually discernible pattern of FIG. 14, but with occasional discontinuous elements 228 forming portions of some of the lines. It will be understood that other lines or portions thereof may also be discontinuous. A distance, D, in a direction parallel to the first line 206, between the third line 210 and the fourth line 212 (or other similar lines) may be the same or may vary.

Figure 18:
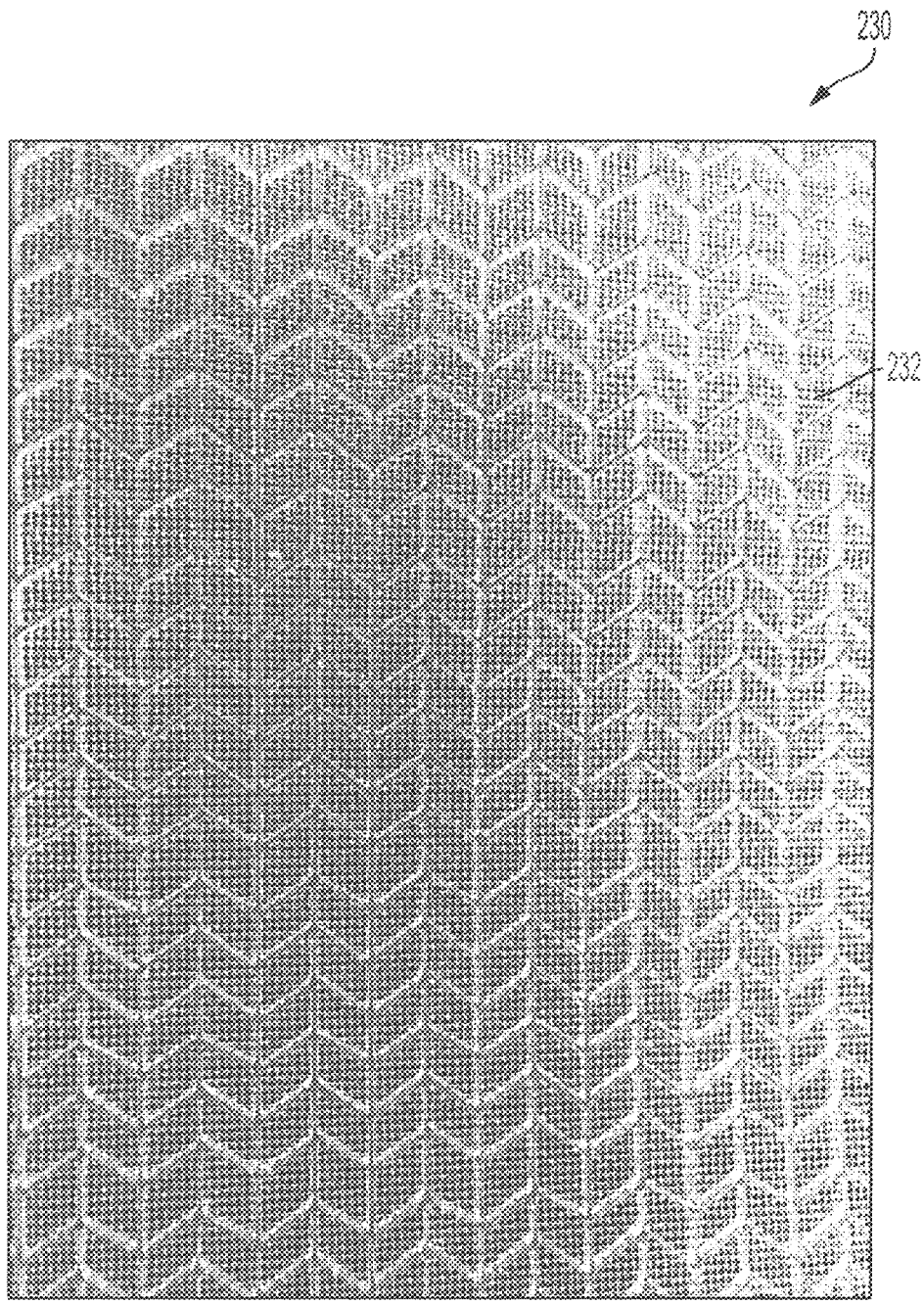
FIG. 18 is a photograph of a portion of a structured forming belt used to create at least some of the nonwoven webs of the present disclosure.
Figure 19:
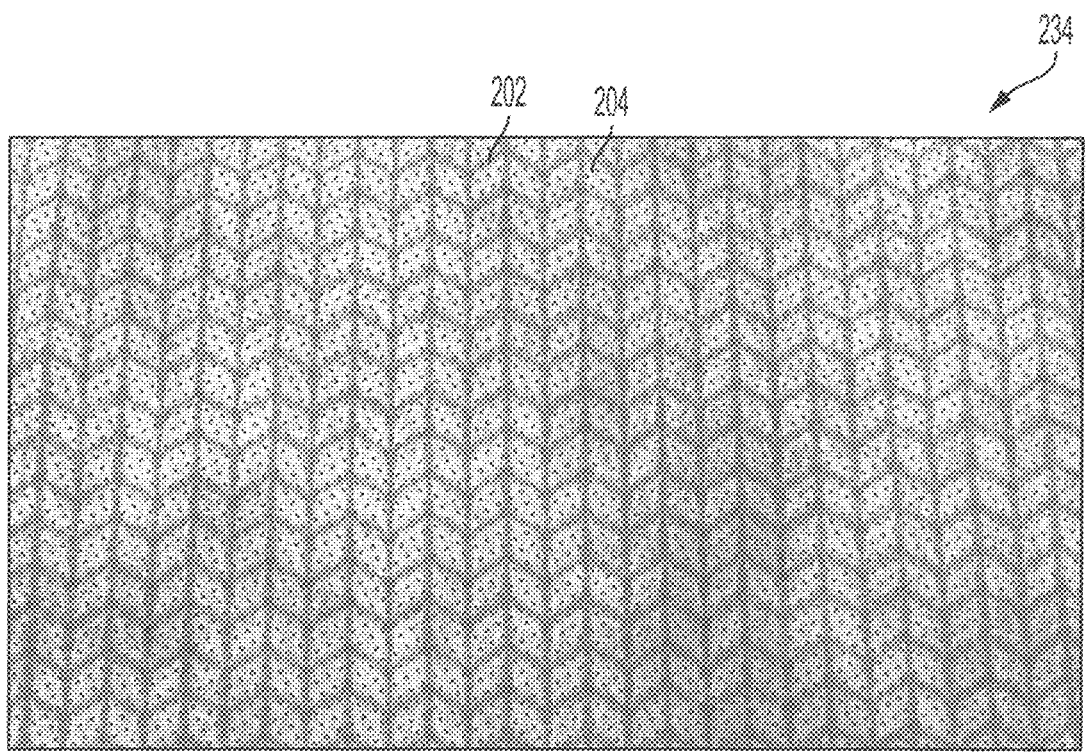
FIG. 19 is a photograph of a portion of a nonwoven web created using the structured forming belt of FIG. 18.

FIG. 18 illustrates a portion of an endless structured forming belt 230 for creating the nonwoven web of FIG. 19 having a visually discernible pattern of three-dimensional features. The forming belt 230 comprises an endless foraminous member 232 comprising a first surface and a second surface. The foraminous member may be an air permeable, woven, wire mesh, for example a plastic wire mesh or other air permeable mesh for foraminous belts known to those of skill in the art. A resin or a curable resin extends outwardly from the first surface of the forming belt 230. The resin may also extend at least partially through the belt. The forming belt 230 comprises a visually discernible pattern of three-dimensional features. The three-dimensional features may comprise one or more first regions 202 and a plurality of second regions 204. The one or more first regions 202 comprise the resin or curable resin and the plurality of second regions 204 are free or, or substantially free of, the resin or curable resin. In other instances, the one or more first regions 202 may be free of, or substantially free of, the resin or curable resin and the plurality of second regions 204 may comprise the resin or curable resin. The one or more first regions 202 of the resin or curable resin may comprise the various lines discussed herein, such as the first line, the second line, the third line, the fourth line, the fifth line, the sixth line, and the seventh line, for example. FIG. 18 is merely one example of a forming belt. It will be understood that other forming belts will be used to create the other patterns illustrated in FIGS. 14-17.

FIG. 19 illustrates a portion of a nonwoven web 234 optionally for an absorbent article comprising a visually discernible pattern of three-dimensional features creating used the forming belt 230 of FIG. 18. The three-dimensional features comprise one or more first regions 202 and a plurality of second regions 204. The one or more first regions 202 of the nonwoven web 234 may comprise the various lines discussed herein, such as the first line, the second line, the third line, the fourth line, the fifth line, the sixth line, and the seventh line, for example.

Any of the nonwoven webs of the present disclosure may be through-air bonded such that bonds occur at individual fiber intersections as hot air is passed through the nonwoven webs. Through-air bonding may help maintain softness in the nonwoven webs compared to more conventional calendar bonding. Other methods of bonding may include calendar point bonding, ultrasonic bonding, latex bonding, hydroentanglement, resin bonding, and/or combinations thereof.

Any of the nonwoven webs of the present disclosure may comprise portions of, or all of, components of absorbent articles. An absorbent article, as discussed above, may comprise a liquid permeable topsheet, a liquid impermeable backsheet, and an absorbent core positioned at least partially intermediate the topsheet and the backsheet. The absorbent article may comprise an outer cover nonwoven material forming at least a portion of a garment-facing surface of the absorbent article. The outer cover nonwoven material and/or the topsheet may comprise the nonwoven webs of the present disclosure. Other components of absorbent articles, or portions thereof, may also comprise the nonwoven webs of the present disclosure, such as leg cuffs, waist cuffs, belts, landing zones, waistbands, and/or ears, for example.

A nonwoven web for an absorbent article is provided. The nonwoven web may comprise a first surface, a second surface, and a visually discernible pattern of three-dimensional features on the first surface or the second surface. The three-dimensional features may comprise one or more first regions and a plurality of second regions. The one or more first regions are different than the plurality of second regions in a value of an average intensive property, wherein the average intensity property is basis weight, volumetric density, and/or caliper. The one or more first regions may comprise a first line extending in a first direction, a second line extending in the first direction, and a third line extending at least partially intermediate the first line and the second line. The third line may extend in a direction transverse to the first line and the second line.

The nonwoven webs comprising the visually discernable patterns of three-dimensional features may have a basis weight in the range of about 10 gsm to about 100 gsm, about 10 gsm to about 60 gsm, about 15 gsm to about 50 gsm, about 15 gsm to about 45 gsm, about 20 gsm to about 40 gsm, about 20 gsm to about 35 gsm, about 20 gsm to about 30 gsm, according to the Basis Weight Test herein, and specifically reciting all 0.1 gsm increments within the specified ranges and all ranges formed therein or thereby.

The visually discernable pattern of three-dimensional features may be formed in a nonwoven web by embossing, hydroentangling, or by using a structured forming belt for fiber laydown. Using embossing or hydroentangling, the first regions or the second regions may be embossed or hydroentangled to form the pattern. The structured forming belt is discussed herein.

Materials

The nonwoven webs of the present disclosure may be formed by a dry-laid process using short staple fibers and mechanical web formation, such as a carding process. The resulting webs may be bonded using irregular pattern thermal embossing or hydroforming/hydroentangling processes. The nonwoven webs may also comprise cotton or other natural fibers. The nonwoven webs of the present disclosure may also be coform webs. Coformed webs typically comprise a matrix of meltblown fibers mixed with at least one additional fibrous organic materials, such as fluff pulp, cotton, and/or rayon, for example. The coform webs may be further structured by embossing or laying down the composite on a structured belt during a coforming process. In an instance, continuous spunbond filaments are used in producing the nonwoven webs if the nonwoven webs are being made on a structured forming belt (as described below). The nonwoven webs may comprise continuous mono-component polymeric filaments comprising a primary polymeric component. The nonwoven webs may comprise continuous multicomponent polymeric filaments comprising a primary polymeric component and a secondary polymeric component. The filaments may be continuous bicomponent filaments comprising a primary polymeric component A and a secondary polymeric component B. The bicomponent filaments have a cross-section, a length, and a peripheral surface. The components A and B may be arranged in substantially distinct zones across the cross-section of the bicomponent filaments and may extend continuously along the length of the bicomponent filaments. The secondary component B constitutes at least a portion of the peripheral surface of the bicomponent filaments continuously along the length of the bicomponent filaments. The polymeric components A and B may be melt spun into multicomponent fibers on conventional melt spinning equipment. The equipment may be chosen based on the desired configuration of the multicomponent. Commercially available melt spinning equipment is available from Hills, Inc.: located in Melbourne, Fla., The temperature for spinning is in the range of about 180° C. to about 230° C. The bicomponent spunbond filaments may have an average diameter from about 6 microns to about 40 microns or from about 12 microns to about 40 microns, for example.

The components A and B may be arranged in either a side-by-side arrangement as shown in FIG. 20A or an eccentric sheath/core arrangement as shown in FIG. 20B to obtain filaments which exhibit a natural helical crimp. Alternatively, the components A and B may be arranged in a concentric sheath/core arrangement as shown in FIG. 20C, Additionally, the component A and B may be arranged in multi-lobal sheath/core arrangement as shown in FIG. 21. Other multicomponent fibers may be produced by using the compositions and methods of the present disclosure. The bicomponent and multicomponent fibers may be segmented pie, ribbon, islands-in-the-sea configurations, or any combination thereof. The sheath may be continuous or non-continuous around the core. The fibers of the present disclosure may have different geometries that comprise round, elliptical, star shaped, rectangular, and other various geometries. Methods for extruding multicomponent polymeric filaments into such arrangements are generally known to those of ordinary skill in the art.

A wide variety of polymers are suitable to practice the present disclosure including polyolefins (such as polyethylene, polypropylene and polybutylene), polyesters, polyamides, polyurethanes, elastomeric materials and the like, Non-limiting examples of polymer materials that can be spun into filaments include natural polymers, such as starch, starch derivatives, cellulose and cellulose derivatives, hemicellulose, hemicelluloses derivatives, chitin, chitosan, polyisoprene (cis and trans), peptides, polyhydroxyalkanoates, and synthetic polymers including, but not limited to, thermoplastic polymers, such as polyesters, nylons, polyolefins such as polypropylene, polyethylene, polyvinyl alcohol and polyvinyl alcohol derivatives, sodium polyacrylate (absorbent gel material), and copolymers of polyolefins such as polyethylene-octene or polymers comprising monomeric blends of propylene and ethylene, and biodegradable or compostable thermoplastic polymers such as polylactic acid filaments, polyvinyl alcohol, filaments, and polycaprolactone filaments. In one example, thermoplastic polymer selected from the group of: polypropylene, polyethylene, polyester, polylactic acid, polyhydroxyalkanoate, polyvinyl alcohol, polycaprolactone, styrene-butadiene-styrene block copolymer, styrene-isoprene-styrene block copolymer, polyurethane, and mixtures thereof. In another example, the thermoplastic polymer is selected from the group consisting of: polypropylene, polyethylene, polyester, polylactic acid, polyhydroxyalkanoate, polyvinyl alcohol, polycaprolactone, and mixtures thereof. Alternatively, the polymer can comprise one derived from monomers which are bio-based such as bio-polyethylene, bio-polypropylene, bio-PET, or PLA, for example.

Primary component A and secondary component B may be selected so that the resulting bicomponent filament provides improved nonwoven bonding and softness. Primary polymer component A may have melting temperature which is lower than the melting temperature of secondary polymer component B.

Primary polymer component A may comprise polyethylene, polypropylene or random copolymer of propylene and ethylene. Secondary polymer component B may comprise polypropylene or random copolymer of propylene and ethylene. Polyethylenes may comprise linear low density polyethylene and high density polyethylene. In addition, secondary polymer component B may comprise polymers, additives for enhancing the natural helical crimp of the filaments, lowering the bonding temperature of the filaments, and enhancing the abrasion resistance, strength and softness of the resulting fabric.

Inorganic fillers, such as the oxides of magnesium, aluminum, silicon, and titanium, for example, may be added as inexpensive fillers or processing aides. Pigments and/or color melt additives may also be added.

The fibers of the nonwoven webs disclosed herein may comprise a slip additive in an amount sufficient to impart the desired haptics to the fiber. As used herein, "slip additive" or "slip agent" means an external lubricant. The slip agent when melt-blended with the resin gradually exudes or migrates to the surface during cooling or after fabrication, hence forming a uniform, invisibly thin coating, thereby yielding permanent lubricating effects. The slip agent may be a fast bloom slip agent.

During the making or in a post-treatment or even in both, the nonwoven webs of the present disclosure may be treated with surfactants or other agents to either hydrophilize the web or make it hydrophobic. For example, a nonwoven web used as a topsheet may be treated with a hydrophilizing material or surfactant so as to make it permeable to body exudates, such as urine and menses. For other absorbent articles, the nonwoven webs may remain in their naturally hydrophobic state or made even more hydrophobic through the addition of a hydrophobizing material or surfactant.

Suitable materials for preparing the multicomponent filaments of the nonwoven webs of the present disclosure may comprise PP3155 polypropylene obtained from Exxon Mobil Corporation and PP3854 polypropylene obtained from Exxon Mobil Corporation.

Structured Forming Belts and Process for Producing Nonwoven Webs

As mentioned above, the nonwoven webs of the present disclosure may be produced by embossing, hydroentangling, or by using a structured forming belt for fiber or filament laydown. The structured forming belt and the process of manufacture will be described now in more detail than above. The nonwoven webs may be formed directly on the structured forming belt with continuous spunbond filaments in a single forming process. The nonwoven webs may assume a shape and texture which corresponds to the shape and texture of the structured forming belt (see e.g., FIGS. 18 and 19).

The present disclosure may utilize the process of melt spinning. Melt spinning may occur from about 150° C. to about 280° or from about 190° to about 230°, for example. Fiber spinning speeds may be greater than 100 meters/minute, from about 1,000 to about 10,000 meters/minute, from about 2,000 to about 7,000 meters/minute, or from about 2,500 to about 5,000 meters/minute, for example. Spinning speeds may affect the brittleness of the spun fiber, and, in general, the higher the spinning speed, the less brittle the fiber. Continuous fibers may be produced through spunbond methods or meltblowing processes.

Figure 22:
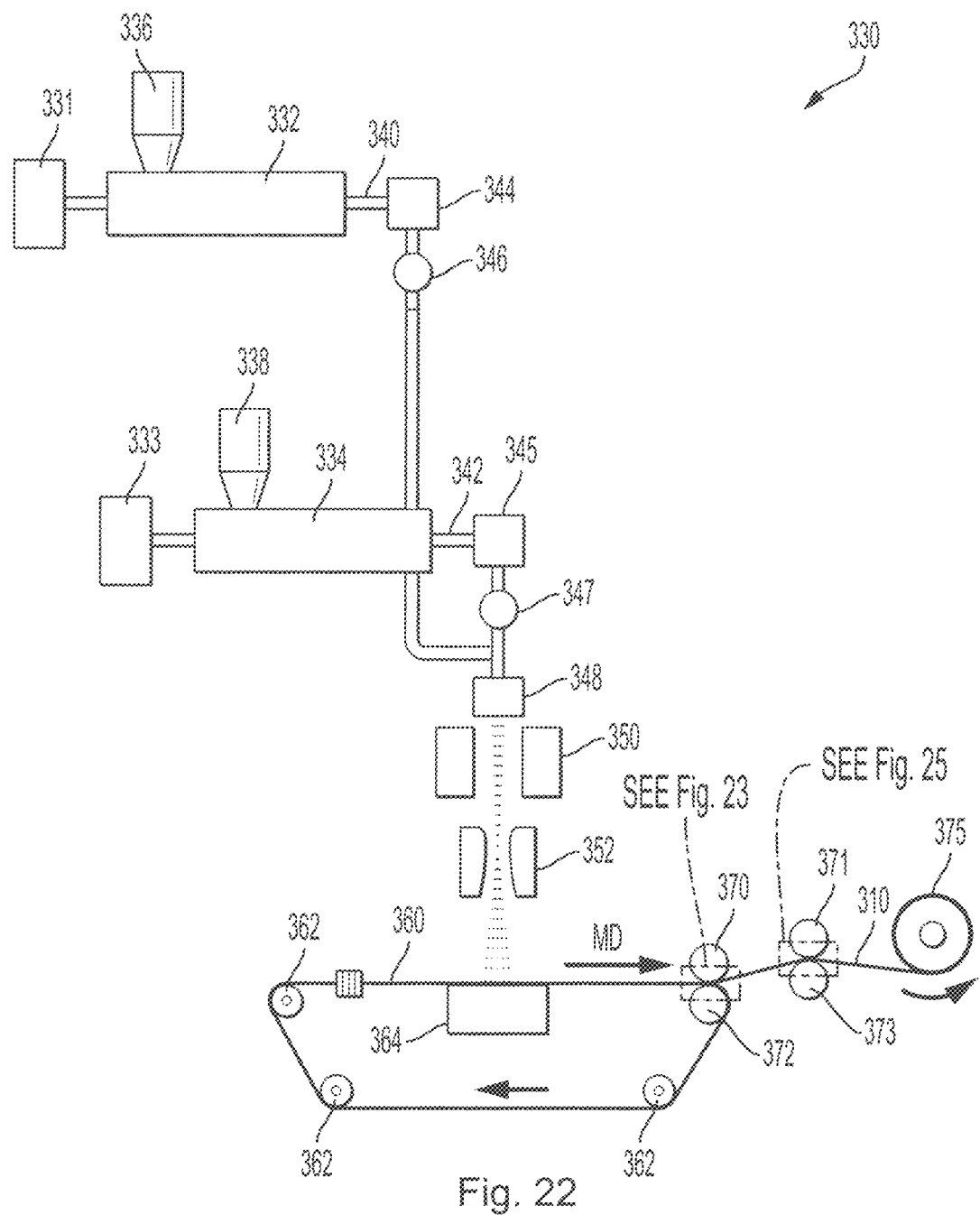
FIG. 22 is a schematic representation of an example apparatus for making the nonwoven webs of the present disclosure.

Referring to FIG. 22, a representative process line 330 for manufacturing some example nonwoven webs made on a structured forming belt of the present disclosure is illustrated. The process line 330 is arranged to produce a nonwoven web of bicomponent continuous filaments, but it should be understood that the present disclosure comprehends nonwoven webs made with monocomponent or multicomponent filaments having more than two components. The bicomponent filaments may or may not be trilobal.

The process line 330 may comprise a pair of extruders 332 and 334 driven by extruder drives 331 and 333, respectively, for separately extruding the primary polymer component A and the secondary polymer component B. Polymer component A may be fed into the respective extruder 332 from a first hopper 336 and polymer component B may be fed into the respective extruder 334 from a second hopper 338. Polymer components A and B may be fed from the extruders 332 and 334 through respective polymer conduits 340 and 342 to filters 344 and 345 and melt pumps 346 and 347, which pump the polymer into a spin pack 348. Spinnerets for extruding bicomponent filaments are generally known to those of ordinary skill in the art.

Generally described, the spin pack 348 comprises a housing which comprises a plurality of plates stacked one on top of the other with a pattern of openings arranged to create flow paths for directing polymer components A and B separately through the spinneret. The spin pack 348 has openings arranged in one or more rows. The spinneret openings form a downwardly extending curtain of filaments when the polymers are extruded through the spinneret. For the purposes of the present disclosure, spinnerets may be arranged to form side-by-side, eccentric sheath/core, or sheath/core bicomponent filaments as illustrated in FIGS. 20A-20C, as well as non-round fibers, such as tri-lobal fibers as shown in FIG. 21. Moreover, the fibers may be mono-component having one polymeric component, such as polypropylene, for example.

The process line 330 may comprises a quench blower 350 positioned adjacent to the curtain of filaments extending from the spinneret. Air from the quench air blower 350 may quench the filaments extending from the spinneret. The quench air may be directed from one side of the filament curtain or both sides of the filament curtain.

An attenuator 352 may be positioned below the spinneret and receives the quenched filaments. Fiber draw units or aspirators for use as attenuators in melt spinning polymers are generally known to those of skill in the art. Suitable fiber draw units for use in the process of forming the nonwoven webs of the present disclosure may comprise a linear fiber attenuator of the type shown in U.S. Pat. No. 3,802,817 and eductive guns of the type shown in U.S. Pat. Nos. 3,692,618 and 3,423,266.

Generally described, the attenuator 352 may comprise an elongate vertical passage through which the filaments are drawn by aspirating air entering from the sides of the passage and flowing downwardly through the passage. A structured, endless, at least partially foraminous, forming belt 360 may be positioned below the attenuator 352 and may receive the continuous filaments from the outlet opening of the attenuator 352. The forming belt 360 may travel around guide rollers 362. A vacuum 364 positioned below the structured forming belt 360 where the filaments are deposited draws the filaments against the forming surface. Although the forming belt 360 is shown as a belt in FIG. 22, it should be understood that the forming belt may also be in other forms such as a drum. Details of particular shaped forming belts are explained below.

In operation of the process line 330, the hoppers 336 and 338 are filled with the respective polymer components A and B. Polymer components A and B are melted and extruded by the respective extruders 332 and 334 through polymer conduits 340 and 342 and the spin pack 348. Although the temperatures of the molten polymers vary depending on the polymers used, when polyethylenes are used as primary component A and secondary component B respectively, the temperatures of the polymers may range from about 190° C. to about 240° C., for example.

As the extruded filaments extend below the spinneret, a stream of air from the quench blower 350 at least partially quench the filaments, and, for certain filaments, to induce crystallization of molten filaments. The quench air may flow in a direction substantially, perpendicular to the length of the filaments at a temperature of about 0° C. to about 35° C. and a velocity from about 100 to about 400 feet per minute. The filaments may be quenched sufficiently before being collected on the forming belt 360 so that the filaments may be arranged by the forced air passing through the filaments and the forming belt 360. Quenching the filaments reduces the tackiness of the filaments so that the filaments do not adhere to one another too tightly before being bonded and may be moved or arranged on the forming belt 360 during collection of the filaments on the forming belt 360 and formation of the nonwoven web.

After quenching, the filaments are drawn into the vertical passage of the attenuator 352 by a flow of the fiber draw unit. The attenuator may be positioned 30 to 60 inches below the bottom of the spinneret.

The filaments may be deposited through the outlet opening of the attenuator 352 onto the shaped, traveling forming belt 360. As the filaments are contacting the forming surface of the forming belt 360, the vacuum 364 draws the air and filaments against the forming belt 360 to form a nonwoven web of continuous filaments which assumes a shape corresponding to the shape of the structured forming surface of the structured forming belt 360. As discussed above, because the filaments are quenched, the filaments are not too tacky and the vacuum may move or arrange the filaments on the forming belt 360 as the filaments are being collected on the forming belt 330 and formed into nonwoven webs.

The process line 330 may comprise one or more bonding devices such as the cylinder-shaped compaction rolls 370 and 372, which form a nip through which the nonwoven web may be compacted (e.g., calendared) and which may be heated to bond fibers as well. One or both of compaction rolls 370, 372 may be heated to provide enhanced properties and benefits to the nonwoven webs by bonding portions of the nonwoven webs. For example, it is believed that heating sufficient to provide thermal bonding improves the nonwoven web's tensile properties. The compaction rolls may be pair of smooth surface stainless steel rolls with independent heating controllers. The compaction rolls may be heated by electric elements or hot oil circulation. The gap between the compaction rolls may be hydraulically controlled to impose desired pressure on the nonwoven web as it passes through the compaction rolls on the forming belt. As an example, with a forming belt caliper of 1.4 mm, and a spunbond nonwoven web having a basis weight of 25 gsm, the nip gap between the compaction rolls 370 and 372 may be about 1.4 mm.

Figure 23:
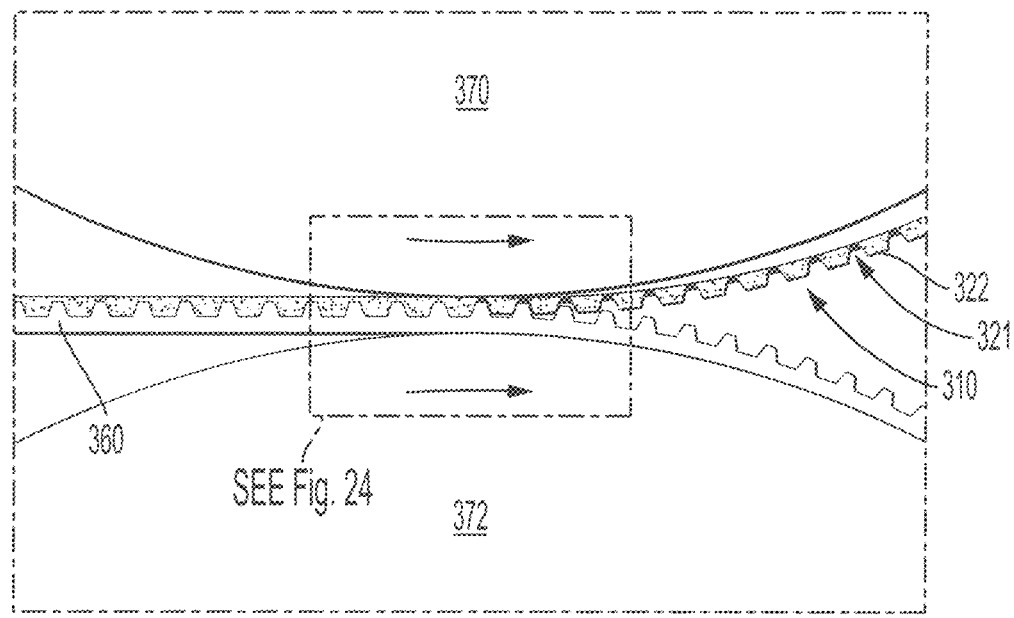
FIG. 23 is a detail of a portion of the apparatus of FIG. 22 for bonding a portion of the nonwoven webs of the present disclosure.
Figure 24:
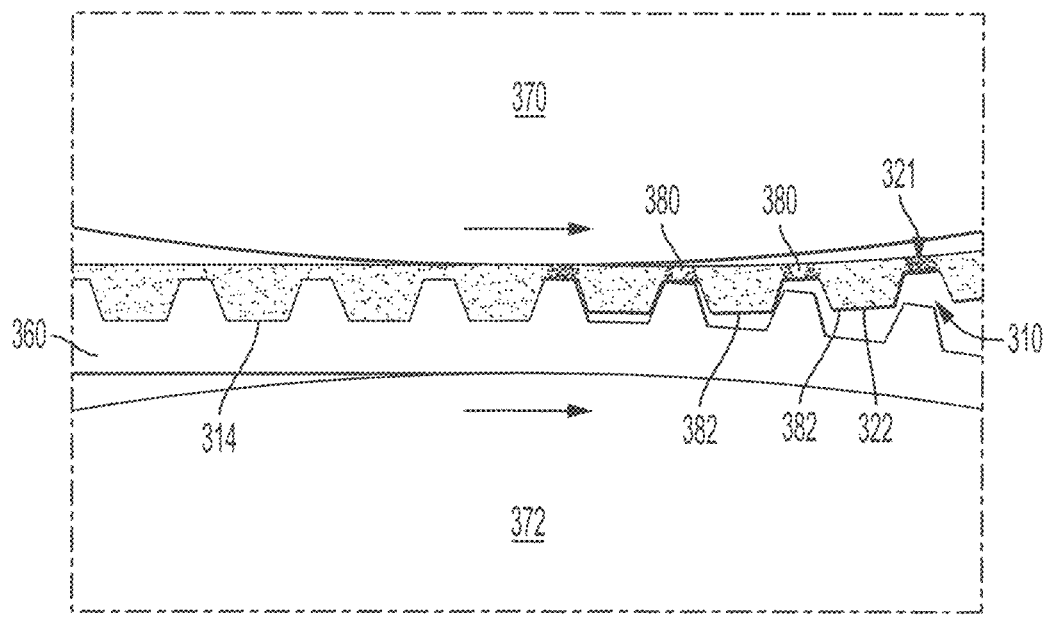
FIG. 24 is a further detail of a portion of the apparatus for bonding a portion of the nonwoven webs of the present disclosure, taken from detail FIG. 24 in FIG. 23.

An upper compaction roll 370 may be heated sufficiently to consolidate or melt fibers on a first surface of a nonwoven web 310, to impart strength to the nonwoven web so that it may be removed from forming belt 360 without losing integrity. As shown in FIGS. 23 and 24, for example, as rolls 370 and 372 rotate in the direction indicated by the arrows, the forming belt 360 with the spunbond web laid down on it enter the nip formed by rolls 370 and 372. Heated roll 370 may, heat the portions of the nonwoven web 310 that are pressed against it by the raised resin elements of belt 360 i.e., in regions 321, to create bonded fibers 380 on at least the first surface of the nonwoven web 310. As can be understood by the description herein, the bonded regions so formed may take the pattern of the raised elements of forming belt 360. By adjusting temperature and dwell time, the bonding may be limited primarily to fibers closest to the first surface of the nonwoven web 310, or thermal bonding may be achieved to a second surface. Bonding may also be a discontinuous network, for example, as point bonds 390, discussed below.

The raised elements of the forming belt 360 may be selected to establish various network characteristics of the forming belt and the bonded regions of the nonwoven web 310. The network corresponds to resin making up the raised elements of the forming belt 360 and may comprise substantially continuous, substantially semi-continuous, discontinuous, or combinations thereof options. These networks may be descriptive of the raised elements of the forming belt 360 as it pertains to their appearance or make-up in the X-Y planes of the forming belt 360 or the three-dimensional features of the nonwoven webs 310.

Figure 25:
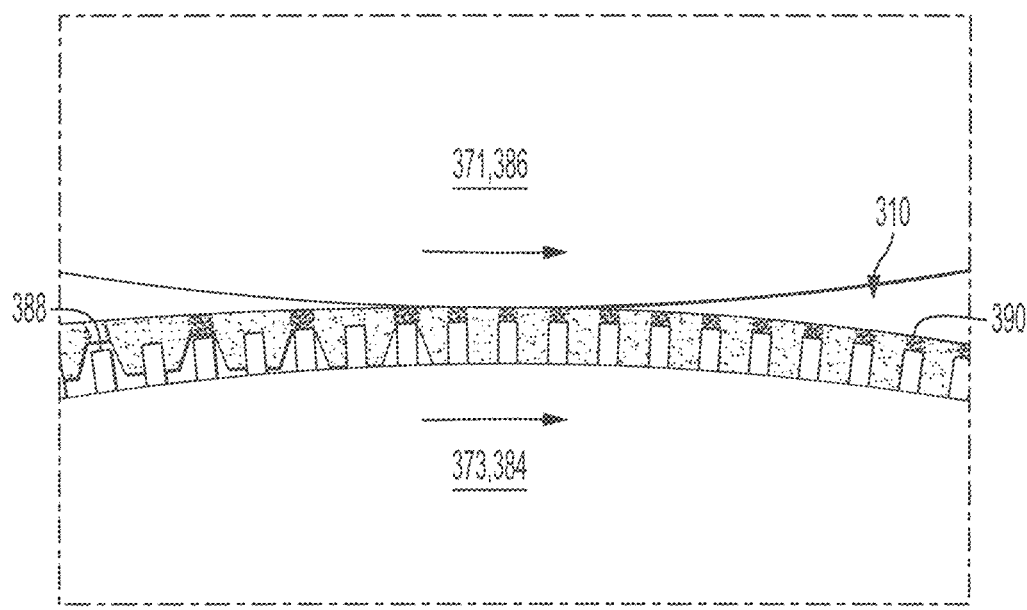
FIG. 25 is a detail of a portion of the apparatus for optional additional bonding of a portion of the nonwoven webs of the present disclosure.
Figure 26:
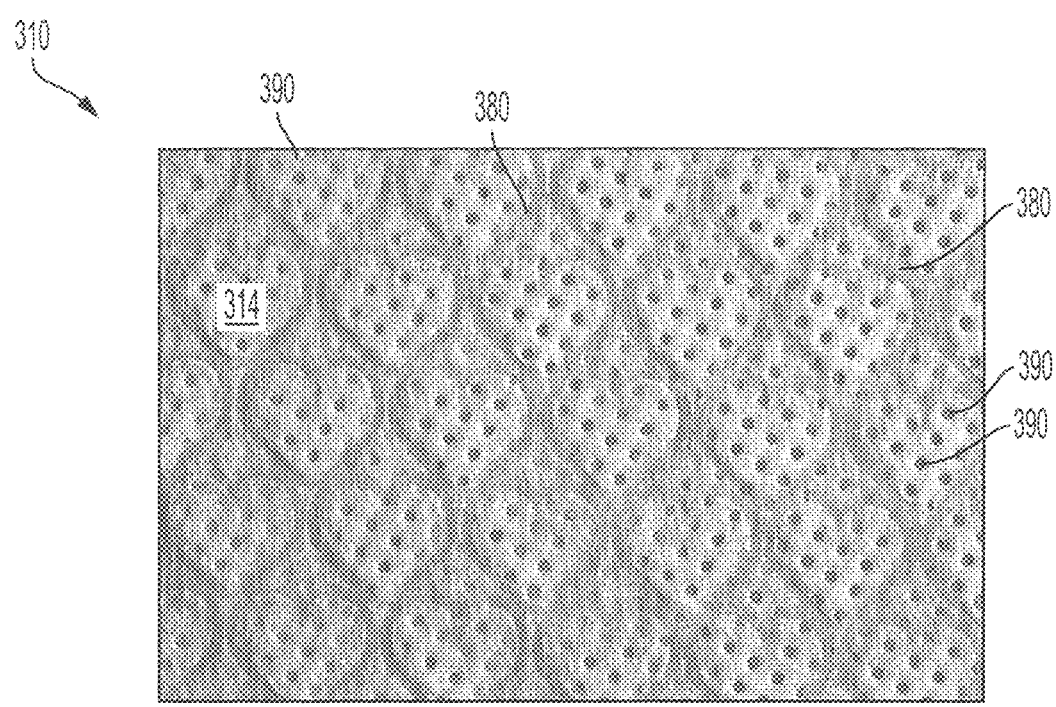
FIG. 26 is a photograph of an example nonwoven web with a different design than the nonwoven webs of the present disclosure.

After compaction, the nonwoven web 310 may leave the forming belt 360 and be calendared through a nip formed by calendar rolls 371, 373, after which the nonwoven web 310 may be wound onto a reel 375 or conveyed directly into a manufacturing operation for products, such as absorbent articles. As shown in the schematic cross-section of FIG. 25, the calendar rolls 371, 373 may be stainless steel rolls having an engraved pattern roll 384 and a smooth roll 386. The engraved roll may have raised portions 388 that may provide for additional compaction and bonding to the nonwoven web 310. Raised portions 388 may be a regular pattern of relatively small spaced apart "pins" that form a pattern of relatively small point bonds 390 in the nip of calendar rolls 371 and 373. The percent of point bonds in the nonwoven web 10 may be from about 3% to about 30% or from about 7% to about 20%, for example. The engraved pattern may be a plurality of closely spaced, regular, generally cylindrically-shaped, generally flat-topped pin shapes, with pin heights being in a range of about 0.5 mm to about 5 mm or from about 1 mm to about 3 mm, for example, Pin bonding calendar rolls may form closely spaced, regular point bonds 390 in the nonwoven web 10, as shown in an example in FIG. 26. Further bonding may be by hot-air-through bonding, for example. FIG. 26 shows a hearts pattern made by the same structured forming belt technology that may be used to make the nonwoven webs of the present disclosure. FIG. 26 is only an example of a pattern, although the visually discernable patterns comprising the three-dimensional features shown, for example, in FIGS. 13-19, are more applicable to the present disclosure.

"Point bonding", as used herein, is a method of thermally bonding a nonwoven web. This method comprises passing a web through a nip between two rolls comprising a heated male patterned or engraved metal roll and a smooth or patterned metal roll. The male patterned roll may have a plurality of raised, generally cylindrical-shaped pins that produce circular point bonds. The smooth roll may or may not be heated, depending on the application. In a nonwoven manufacturing line, the nonwoven web, which could be a non-bonded nonwoven web, is fed into the calendar nip and the fiber temperature is raised to the point for fibers to thermally fuse with each other at the tips of engraved points and against the smooth roll. The heating time is typically in the order of milliseconds. The nonwoven web properties are dependent on process settings such as roll temperatures, web line speeds, and nip pressures, all of which may be determined by the skilled person for the desired level of point bonding. Other types of point bonding known generally, as hot calendar bonding may use different geometries for the bonds (other than circular shaped), such as oval, lines, circles, for example. In an example, the point bonding produces a pattern of point bonds being 0.5 mm diameter circles with 10% overall bonding area. Other bonding shapes may have raised pins having a longest dimension across the bonding surface of a pin of from about 0.1 mm to 2.0 mm and the overall bonding area ranges from about 5% to about 30%, for example.

As shown in FIG. 26, a heated compaction roll 370 may form a bond pattern, which may be a substantially continuous network bond pattern 380 (e.g., interconnected heart shaped bonds) on a first surface of the nonwoven web 310 (not shown in FIG. 26, as it faces away from the viewer), and the engraved calendar roll 373 may form relatively small point bonds 390 on a second surface 314 of the nonwoven web. The point bonds 390 may secure loose fibers that would otherwise be prone to fuzzing or pilling during use of the nonwoven web 310. The advantage of the resulting structure of the nonwoven web 310 is most evident when used as a topsheet or outer cover nonwoven material in an absorbent article, such as a diaper, for example. In use, in an absorbent article, a first surface of the nonwoven web 310 may be relatively flat (relative to second surface 14) and have a relatively large amount of bonding due to the heated compaction roll forming bonds 380 at the areas of the nonwoven web pressed by the raised elements of the forming belt 360. This bonding gives the nonwoven web 310 structural integrity, but still may be relatively stiff or rough to the skin of a user. Therefore, a first surface of the nonwoven web 310 may be oriented in a diaper or sanitary napkin to face the interior of the article, i.e., away from the body of the wearer or garment-facing. Likewise, the second surface 314 may be wearer-facing in use, and in contact with the body. The relatively small point bonds 390 may be less likely to be perceived visually or tacitly by the user, and the relatively soft three-dimensional features may remain visually free of fuzzing and pilling while feeling soft to the body in use. Further bonding may be used instead of, or in addition to, the above-mentioned bonding. Through-air bonding may also be used.

The forming belt 360 may be made according to the methods and processes described in U.S. Pat. No. 6,610,173, issued to Lindsay et al., on Aug. 26, 2003, or U.S. Pat. No. 5,514,523, issued to Trokhan et al., on May 7, 1996, or U.S. Pat. No. 6,398,910, issued to Burazin et al., on Jun. 4, 2002, or U.S. Pat. No. 8,940,376, issued to Stage et al., on Jan. 27, 2015, each with the improved features and patterns disclosed herein for making spunbond nonwoven webs. The Lindsay, Trokhan, Burazin, and Stage disclosures describe structured forming belts that are representative of papermaking belts made with cured resin on a woven reinforcing member, which belts, with improvements, may be utilized to form the nonwoven webs of the present disclosure as described herein.

Figure 27:
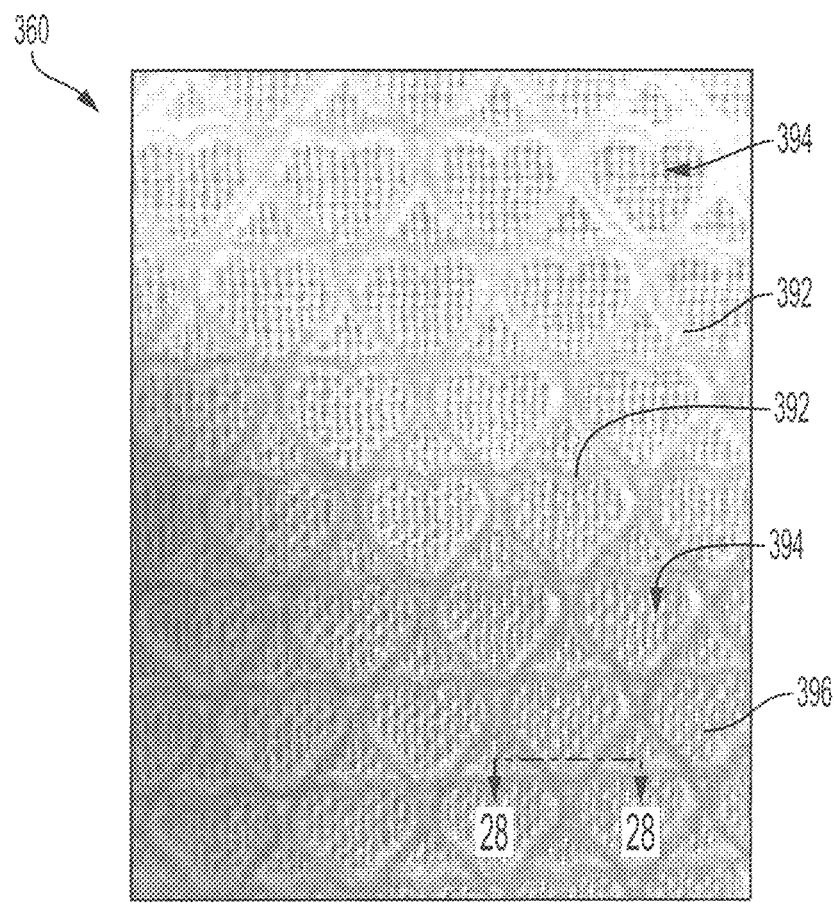
FIG. 27 is a photograph of a portion of a forming belt with the different design for forming nonwoven webs.

An example of a structured forming belt 360, and which may be made according to the disclosure of U.S. Pat. No. 5,514,523, is shown in FIG. 27. As taught therein, a reinforcing member 394 (such as a woven belt of filaments 396) is thoroughly coated with a liquid photosensitive polymeric resin to a preselected thickness. A film or negative mask incorporating the desired raised element pattern repeating elements (e.g., FIG. 29) is juxtaposed on the liquid photosensitive resin. The resin is then exposed to light of an appropriate wave length through the film, such as UV light for a UV-curable resin. This exposure to light causes curing of the resin in the exposed areas (i.e., white portions or non-printed portions in the mask). Uncured resin (resin under the opaque portions in the mask) is removed from the system leaving behind the cured resin forming the pattern illustrated, for example, the cured resin elements 392 shown in FIG. 27. Other patterns may also be formed, such as the patterns illustrated in FIGS. 13 to 19.

Figure 28:
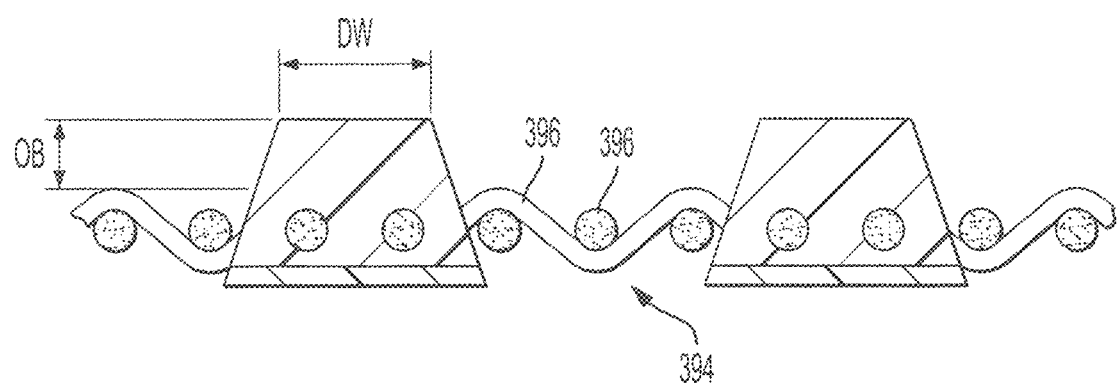
FIG. 28 is a cross-sectional depiction of a portion of the forming belt, taken about line 28-28 of FIG. 27.
Figure 29:
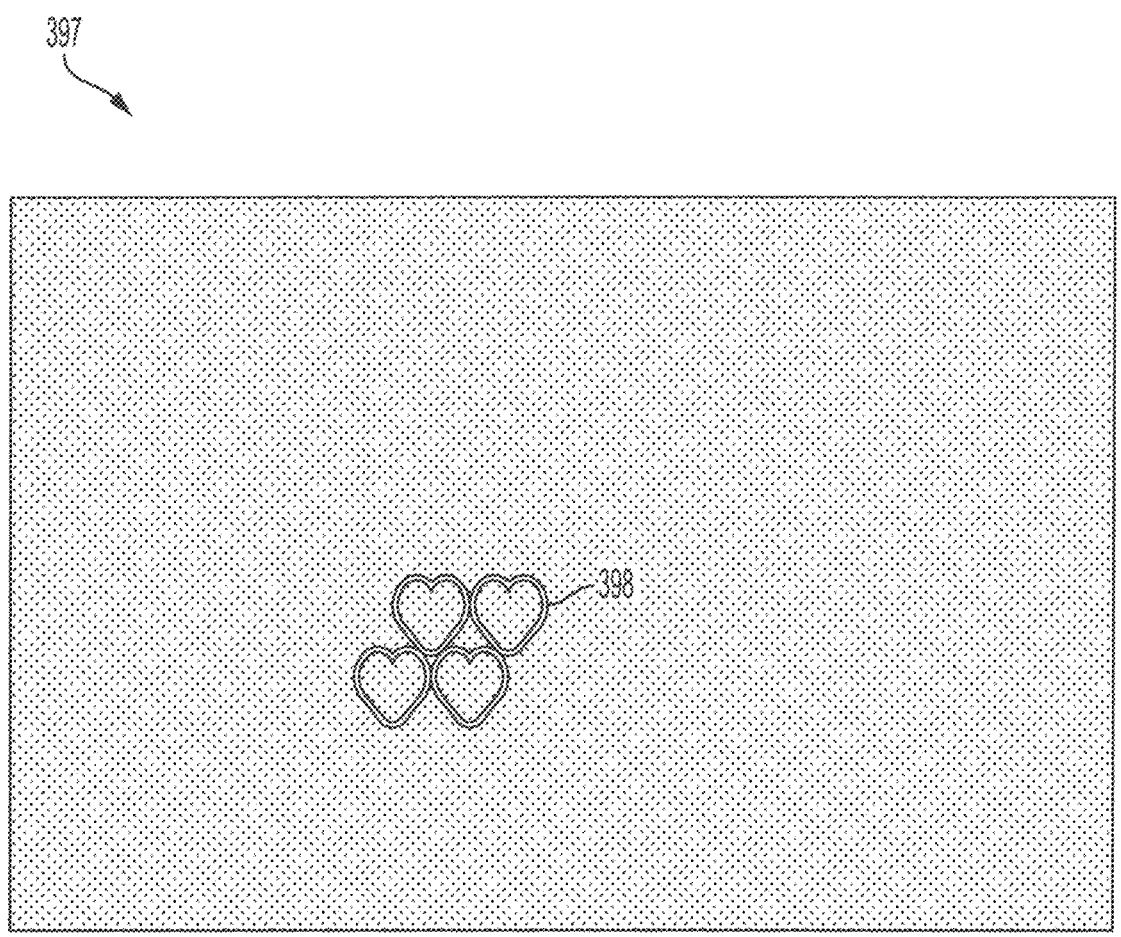
FIG. 29 is an image of a portion of a mask utilized to at least in part create the forming belt of FIG. 27.

The forming belt 360 may comprise cured resin elements 392 on a woven reinforcing member 394. The reinforcing member 394 may be made of woven filaments 396 as is generally known in the art of papermaking belts, including resin coated papermaking belts. The cured resin elements may have the general structure depicted in FIG. 27, and are made by the use of a mask 397 having the dimensions indicated in FIG. 329 As shown in schematic cross-section in FIG. 28, cured resin elements 392 flow around and are cured to "lock on" to the reinforcing member 394 and may have a width at a distal end DW of about 0.020 inches to about 0.060 inches, or from about 0.025 inches to about 0.030 inches, and a total height above the reinforcing member 394, referred to as over burden, OB, of about 0.030 inches to about 0.120 inches or about 0.50 inches to about 0.80 inches, or about 0.040 inches. FIG. 29 represents a portion of a mask 397 showing the design and representative dimensions for one repeat unit of the repeating hearts design, shown herein merely as an example. The white portion 398 is transparent to UV light, and in the process of making the belt, as described in U.S. Pat. No. 5,514,523, permits UV light to cure an underlying layer of resin which is cured to form the raised elements 392 on the reinforcing member 394. After the uncured resin is washed away, the forming belt 360 having a cured resin design as shown in FIG. 27 is produced by seaming the ends of a length of the forming belt, the length of which may be determined by the design of the apparatus, as depicted in FIG. 22.

Figure 30:
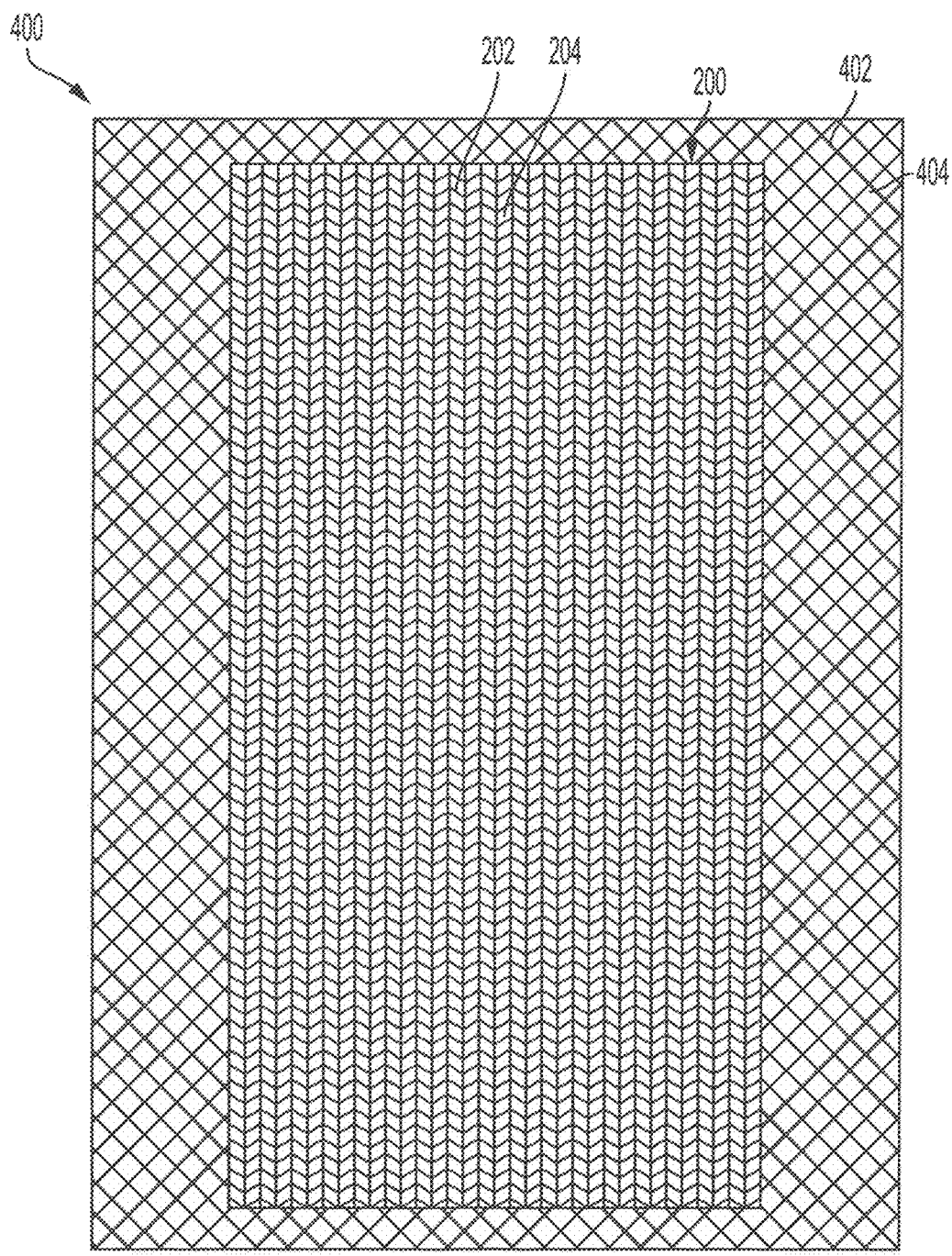
FIG. 30 is an example a nonwoven web having a first visually discernible pattern of three dimensional features and a second visually discernable pattern of three-dimensional features.

The nonwoven webs comprising the visually discernible patterns of three-dimensional features of the present disclosure may also have one or more other visually discernible patterns of three-dimensional features 400, as shown in FIG. 30. While the other patterns may be embossed or hydroentangled, they may also be formed using the structured forming belts described herein and process thereof. The other visually discernible patterns of three-dimensional features 400 may each comprise one or more first regions 402 and a plurality of second regions 404 (visually discernible pattern 400 is merely used as one example). The one or more first regions 402 may have an average intensive property having a first value and the plurality of second regions 404 may have the average intensive property having a second value. The first value may be different than the second value. The average intensive property may be caliper, basis weight, or volumetric density. The other visually discernible patterns of three-dimensional features may include a different pattern of FIGS. 13-19 vs. a completely different pattern as shown in FIG. 30.

The nonwoven webs disclosed herein may be fluid permeable. The entire nonwoven web may be considered fluid permeable or some regions may be fluid permeable. By fluid permeable, as used herein, with respect to the nonwoven web is meant that the nonwoven web has at least one region which permits liquid to pass through under in-use conditions of a consumer product or absorbent article. For example, if used as a topsheet on a disposable absorbent article, the nonwoven web may have at least one zone having a level of fluid permeability permitting urine to pass through to an underlying absorbent core. By fluid permeable, as used herein with respect to a region, it is meant that the region exhibits a porous structure that permits liquid to pass through.

Because of the nature of the structured forming belts and other apparatus elements, as described herein, the three-dimensional features of the nonwoven web have average intensive properties that may differ between first and second regions, or from feature to feature in ways that provide for beneficial properties of the nonwoven web when used in personal care articles, garments, medical products, and cleaning products. For example, a first region may have a basis weight or density that is different from the basis weight or density of a second region, and both may have a basis weight or density that is different from that of a third region, providing for beneficial aesthetic and functional properties related to fluid acquisition, distribution and/or absorption in diapers or sanitary napkins.

The average intensive property differential between the various regions of the nonwoven webs is believed to be due to the fiber distribution and compaction resulting from the apparatus and method described herein. The fiber distribution occurs during the fiber laydown process, as opposed to, for example, a post making process such as embossing processes. Because the fibers are free to move during a process such as a melt spinning process, with the movement determined by the nature of the features and air permeability of the forming belt and other processing parameters, the fibers are believed to be more stable and permanently formed in nonwoven web.

In structured forming belts having multiple zones, the air permeability in each zone may be variable such that the intensive properties of average basis weight and average volumetric density in the zones may be varied. Variable air permeabilities in the various zones causes fiber movement during laydown. The air permeability may be between about 400 to about 1000 cfm, or between about 400 to about 800 cfm, or between about 500 cfm and about 750 cfm, or between about 650 to about 700 cfm, specifically reciting all 1 cfm increments within the specified ranges and all ranges formed therein or thereby.

A structured forming belt may comprise an endless foraminous member comprising a first surface and a second surface, a curable resin extending from the first surface of the foraminous member, and a visually discernible pattern of three-dimensional features on the endless foraminous member. The three-dimensional features may comprise one or more first regions and a plurality of second regions. The one or more first regions may comprise the resin and the plurality of second regions may be free of the resin. The one or more first regions may comprise a first line, a second line extending substantially parallel to the first line, and a third line extending at least partially intermediate the first line and the second line, wherein the third line extends transverse to the first line and the second line. The forming belt may also have a fourth line, a fifth line, a sixth line, a seventh line, and various other lines as explained herein.

Bio-Based Content for Absorbent Article Components

Components of the disposable absorbent article (i.e., diaper, disposable pant, adult incontinence article, sanitary napkin, pantiliner, etc.) described in this specification may at least partially be comprised of bio-sourced content as described in U.S. Pat. Appl. Publ. No. 2007/0219521A1 Hird et al., published on Sep. 20, 2007, U.S. Pat. Appl. Publ. No. 2011/0139658A1 Hird et al., published on Jun. 16, 2011, U.S. Pat. Appl. Publ. No. 2011/0139657A1 Hird et al., published on Jun. 16, 2011, U.S. Pat. Appl. Publ. No 2011/0152812A1 Hird et al., published on Jun. 23, 2011, U.S. Pat. Appl. Publ. No. 2011/0139662A1 Hird et al., published on Jun. 16, 2011, and U.S. Pat. Appl. Publ. No. 2011/0139659A1 Hird et al., published on Jun. 16, 2011. These components include, but are not limited to, topsheet nonwovens, backsheet films, backsheet nonwovens, side panel nonwovens, barrier leg cuff nonwovens, super absorbents, nonwoven acquisition layers, core wrap nonwovens, adhesives, fastener hooks, and fastener landing zone nonwovens and film bases.

In some forms, a disposable absorbent article component comprises a bio-based content value from about 10% to about 100% using ASTM D6866-10, method B, in another embodiment, from about 25% to about 75%, and in yet another embodiment, from about 50% to about 60% using ASTM D6866-10, method B.

In order to apply the methodology of ASTM D6866-10 to determine the bio-based content of any disposable absorbent article component, a representative sample of the disposable absorbent article component must be obtained for testing. In a form, the disposable absorbent article component may be ground into particulates less than about 20 mesh using known grinding methods (e.g., Wiley® mill), and a representative sample of suitable mass taken from the randomly mixed particles.

Nonwoven webs may comprise multicomponent fibers or bicomponent fibers, where at least one or more of the components are bio-based. Examples include side-by-side, sheath/core, or islands in the sea configurations, where one or more or all of the components are bio-based.

Test Methods

Air Permeability Test Method

The Air Permeability Test is used to determine the level of air flow in cubic feet per minute (cfm) through a forming belt. The Air Permeability Test is performed on a Texas Instruments model FX3360 Portair Air Permeability Tester, available from Textest AG, Sonnenbergstrasse 72, CH 8603 Schwerzenbach, Switzerland. The unit utilizes a 20.7 mm orifice plate for air permeability ranges between 300-1000 cfm. If air permeability is lower than 300 cfm the orifice plate needs to be reduced; if higher than 1000 cfm the orifice plate needs to be increased. Air permeability can be measured in localized zones of a forming belt to determine differences in air permeability across a forming belt.

Test Procedure

1. Power on the FX3360 instrument.
2. Select a pre-determined style having the following setup:
    a. Material: Standard
    b. Measurement Property: Air Permeability (AP)
    c. Test Pressure: 125 Pa (pascals)
    d. T-factor: 1.00
    e. Test point pitch: 0.8 inch.
3. Position the 20.7 mm orifice plate on the top side of the forming belt (the side with the three-dimensional protrusions) at the position of interest.
4. Selecting "Spot Measurement" on the touch screen of the testing unit.
5. Reset the sensor prior to measurement, if necessary.
6. Once reset, select the "Start" button to begin measurement.
7. Wait until the measurement stabilizes and record the cfm reading on the screen.
8. Select the "Start" button again to stop measurement.

Basis Weight Test

Basis weight of the nonwoven webs described herein may be determined by several available techniques, but a simple representative technique involves taking an absorbent article or other consumer product, removing any elastic which may be present and stretching the absorbent article or other consumer product to its full length. A punch die having an area of 45.6 cm$^2$ is then used to cut a piece of the nonwoven web (e.g., topsheet, outer cover) from the approximate center of the absorbent article or other consumer product in a location which avoids to the greatest extent possible any adhesive which may be used to fasten the nonwoven web to any other layers which may be present and removing the nonwoven web from other layers (using cryogenic spray, such as Cyto-Freeze, Control Company, Houston, Texas, if needed). The sample is then weighed and dividing by the area of the punch die yields the basis weight of the nonwoven web. Results are reported as a mean of 5 samples to the nearest 0.1 gram per square meter (gsm).

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular forms of the present disclosure have been illustrated and described, it would be obvious to those skilled in the art that various other changes and modifications can be made without departing from the spirit and scope of the present disclosure. It is therefore intended to cover in the appended claims all such changes and modifications that are within the scope of this present disclosure.

What is claimed is:

1. A nonwoven web for an absorbent article, the nonwoven web comprising:
    a first surface;
    a second surface; and
    a visually discernible pattern of three-dimensional features on the first surface or the second surface, wherein the three-dimensional features comprise one or more first regions and a plurality of second regions;
    wherein the one or more first regions have a first value of an average intensive property, wherein the plurality of second regions have a second value of the average intensive property, wherein the first value and the second value are different, and wherein the first value and the second value are greater than zero, wherein the average intensity property is basis weight;
    wherein the one or more first regions comprise:
        a first line;
        a second line, wherein the first line extends in a direction substantially parallel to the second line;
        a third line extending at least partially intermediate the first line and the second line, wherein the third line extends in a direction transverse to the first line and the second line, wherein the third line is curvilinear and comprises an arcuate portion;
        a fourth line extending at least partially intermediate the first line and second line, wherein the fourth line extends in a direction transverse to the first line and the second line, wherein the fourth line is curvilinear and comprises an arcuate portion; and
        a fifth line extending in a direction substantially parallel to the first line, wherein the fifth line is substantially symmetrical to the second line about the first line;
        a sixth line extending transversely at least partially intermediate the first line and the fifth line, wherein the sixth line is symmetrical to the third line about the first line;
        a seventh line extending transversely at least partially intermediate the first line and the fifth line, wherein the sixth line and the seventh line have substantially the same length;
        an eighth line extending in a direction substantially parallel to the first line, wherein the eighth line is substantially parallel to the first line about the fifth line; and
        a ninth line extending transversely at least partially intermediate the fifth line and the eighth line, wherein the ninth line is symmetrical to the sixth line about the fifth line;
        wherein the third, fourth, and ninth lines have a positive slope relative to the first and second lines;
        wherein the sixth and seventh lines have a negative slope relative to the first and second lines;
        wherein the fifth, sixth, and ninth lines intersect at the same point;
        wherein the first, third, and sixth lines intersect at the same point;
        wherein the first, fourth, and seventh lines intersect at the same point; and
    wherein the plurality of second regions are free of the first line, the second line, and the third line.

2. The nonwoven web for an absorbent article of claim 1, wherein the first line is discontinuous, wherein the second line is discontinuous, and wherein the third line is discontinuous.

3. The nonwoven web for an absorbent article of claim 2, wherein the first line comprises a first plurality of first discontinuous elements, wherein the second line comprises a second plurality of second discontinuous elements, and wherein the third line comprises a third plurality of third discontinuous elements.

4. The nonwoven web for an absorbent article of claim 1, wherein the first line and the second line are continuous lines.

5. The nonwoven web for an absorbent article of claim 1, wherein the first line and the second line have a first length, wherein the third line has a second length, wherein the first length is greater than the second length, and wherein the third line and the fourth line have substantially the same length and slope.

6. The nonwoven web for an absorbent article of claim 1, wherein at least some of the one or more first regions fully enclose a second region.

7. The nonwoven web for an absorbent article of claim 1, wherein the nonwoven web comprises bonds at fiber intersections formed by passing hot air through the nonwoven web.

8. The nonwoven web for an absorbent article of claim 1, wherein the nonwoven web comprises a second, visually discernible pattern of three-dimensional features on the first surface or the second surface, wherein the three-dimensional features comprise one or more third regions and a plurality of fourth regions, and wherein the one or more third regions are different than the plurality of fourth regions in a value of an average intensive property, wherein the average intensity property is basis weight.

9. The nonwoven web for an absorbent article of claim 1, wherein the nonwoven web comprises multicomponent fibers, and wherein at least one component of the multicomponent fibers is bio-based.

10. The nonwoven web for an absorbent article of claim 1, wherein the one or more first regions resemble stitching of a quilted fabric, and wherein the plurality of second regions resemble pillows of a quilted fabric.

11. An absorbent article comprising the nonwoven web of any one of the preceding claims.

12. The absorbent article of claim 11, comprising:
    a liquid permeable topsheet;
    a liquid impermeable backsheet;
    an absorbent core positioned intermediate the topsheet and the backsheet;
    an outer cover nonwoven material forming a garment-facing surface of the absorbent article; and
    a front belt.

13. The absorbent article of claim 12, wherein the outer cover nonwoven material comprises the nonwoven web.

14. The absorbent article of claim 12, wherein the liquid permeable topsheet comprises the nonwoven web.

15. The absorbent article of claim 12, wherein the front belt comprises the nonwoven web.

16. A nonwoven web for an absorbent article, the nonwoven web comprising:
- a first surface;
- a second surface;
- a plurality of continuous spunbond fibers; and
- a visually discernible pattern of three-dimensional features on the first surface or the second surface, wherein the three-dimensional features comprise one or more first regions and a plurality of second regions;
- wherein the one or more first regions have a first value of an average intensive property, wherein the plurality of second regions have a second value of the average intensive property, wherein the first value and the second value are different, wherein the first value and the second value are greater than zero, and wherein the average intensity property is basis weight;
- wherein the one or more first regions comprise:
  - a first line extending in a first direction;
  - a second line extending in the first direction, wherein the first line extends in a direction substantially parallel to the second line;
  - a third line extending at least partially intermediate the first line and the second line, wherein the third line extends in a direction transverse to the first direction, wherein the third line is curvilinear and comprises an arcuate portion;
  - a fourth line extending at least partially intermediate the first line and second line, wherein the fourth line extends in a direction transverse to the first line and the second line, wherein the fourth line is curvilinear and comprises an arcuate portion;
  - a fifth line extending in a direction substantially parallel to the first line, wherein the fifth line is substantially symmetrical to the second line about the first line;
  - a sixth line extending transversely at least partially intermediate the first line and the fifth line, wherein the sixth line is symmetrical to the third line about the first line;
  - a seventh line extending transversely at least partially intermediate the first line and the fifth line, wherein the sixth line and the seventh line have substantially the same length;
  - an eighth line extending in a direction substantially parallel to the first line, wherein the eighth line is substantially parallel to the first line about the fifth line; and
  - a ninth line extending transversely at least partially intermediate the fifth line and the eighth line, wherein the ninth line is symmetrical to the sixth line about the fifth line;
  - wherein the third, fourth, and ninth lines have a positive slope relative to the first and second lines;
  - wherein the sixth and seventh lines have a negative slope relative to the first and second lines;
  - wherein the fifth, sixth, and ninth lines intersect at the same point;
  - wherein the first, third, and sixth lines intersect at the same point;
  - wherein the first, fourth, and seventh lines intersect at the same point; and
  - wherein the plurality of second regions are free of the first line, the second line, and the third line.

17. A nonwoven web for an absorbent article, the nonwoven web comprising:
- a first surface;
- a second surface; and
- a visually discernible pattern of three-dimensional features on the first surface or the second surface, wherein the three-dimensional features comprise one or more first regions and a plurality of second regions;
- wherein the one or more first regions are different than the plurality of second regions in a value of an average intensive property;
- wherein the one or more first regions comprise:
  - a first line;
  - a second line, wherein the first line extends in a direction substantially parallel to the second line;
  - a third line extending at least partially intermediate the first line and the second line, wherein the third line extends in a direction transverse to the first line and the second line, wherein the third line is curvilinear;
  - a fourth line extending at least partially intermediate the first line and second line, wherein the fourth line extends in a direction transverse to the first line and the second line, wherein the fourth line is curvilinear;
  - a fifth line extending in a direction substantially parallel to the first line, wherein the fifth line is substantially symmetrical to the second line about the first line;
  - a sixth line extending transversely at least partially intermediate the first line and the fifth line, wherein the sixth line is symmetrical to the third line about the first line;
  - a seventh line extending transversely at least partially intermediate the first line and the fifth line, wherein the sixth line and the seventh line have substantially the same length;
  - an eighth line extending in a direction substantially parallel to the first line, wherein the eighth line is substantially parallel to the first line about the fifth line; and
  - a ninth line extending transversely at least partially intermediate the fifth line and the eighth line, wherein the ninth line is symmetrical to the sixth line about the fifth line
  - wherein the third, fourth, and ninth lines have a positive slope relative to the first and second lines;
  - wherein the sixth and seventh lines have a negative slope relative to the first and second lines;
  - wherein the fifth, sixth, and ninth lines intersect at the same point;
  - wherein the first, third, and sixth lines intersect at the same point;
  - wherein the first, fourth, and seventh lines intersect at the same point; and;
- a second visually discernible pattern of three-dimensional features on the first surface or the second surface, wherein the three-dimensional features comprise one or more third regions and a plurality of fourth regions, and wherein the one or more third regions are different than the plurality of fourth regions in a value of the average intensive property, wherein the average intensity property is basis weight;
- wherein the plurality of second regions are free of the first line, the second line, and the third line.

* * * * *